United States Patent [19]

Hercend et al.

[11] Patent Number: 5,798,231
[45] Date of Patent: Aug. 25, 1998

[54] NUCLEOTIDE SEQUENCES FOR α CHAIN VARIABLE REGIONS IN HUMAN LYMPHOCYTE RECEPTORS, CORRESPONDING PEPTIDE SEGMENTS AND THE DIAGNOSTIC AND THERAPEUTIC USES

[75] Inventors: Thierry Hercend, Nogent-sur Marne; Frederic Triebel, Seine; Sergio Roman-Roman; Laurent Ferradini, both of Paris, all of France

[73] Assignee: Roussel Uclaf, France

[21] Appl. No.: 620,467

[22] Filed: Mar. 22, 1996

Related U.S. Application Data

[62] Division of Ser. No. 348,572, Apr. 19, 1995, which is a continuation of Ser. No. 934,529, Nov. 24, 1992, abandoned.

[30] Foreign Application Priority Data

Feb. 8, 1991 [FR] France .................... 91 01487
Apr. 12, 1991 [FR] France .................... 91 04527

[51] Int. Cl.⁶ .................... C12P 19/34; C12Q 1/68; C07H 21/04

[52] U.S. Cl. .................... 435/91.2; 435/6; 435/810; 536/24.31; 536/24.33; 935/8; 935/77; 935/78

[58] Field of Search .................... 435/6, 91.2; 935/8, 935/77, 78; 536/23.1–23.53, 24.31, 24.33

[56] References Cited

FOREIGN PATENT DOCUMENTS 0200350  11/1986  European Pat. Off.

OTHER PUBLICATIONS

Klein et. al. P.N.A.S. USA 84:6884–6888 (Oct. 1987).
Roman–Roman et. al. Eur. J. Immunol 21:927–933 (Apr. 1991).
Sottini et. al. Eur. J. Immunol 21:461–466 (Feb. 1991).

*Primary Examiner*—W. Gary Jones
*Assistant Examiner*—Debra Shoemaker
*Attorney, Agent, or Firm*—Bierman, Muserlian and Lucas

[57] ABSTRACT

The present invention relates to new nucleotide sequences coding for variable regions of the α chains of human T lymphocyte receptors, corresponding peptide segments and the diagnostic and therapeutic uses.

9 Claims, 5 Drawing Sheets

FIG. 1A

```
Vα1              1
IGRa08    AGTGTTTCCCTTGCTCTCAGCCATGCTCCTCCTGGAGCTTATCCCACTGCTGGGGATACATTTGTCCTGAGAACTGCCAGAGCCCAGTCAGTGACCCAGCCTGA
IGRa08    CATCCACATCACTGTCTCTGAAGGAGCCTCACTGGAGTTGAGATGTAACTATTCCTATGGGGCAACACCTTATCTCTTCTGGTATGTCCAGTCCCCCGGC
IGRa08    CAAGGCCTCCAGTGCCTGCTCCTGGAGACACTCTGGTTCAAGGCATTAAAGGCTTTGAGGCTGAATTTAAGAGGAGTCAATCTTCCTTCA
IGRa08    ACCTGAGGAAACCCTGTGTGCATTGGAGTGATGCTGCTGAGTACTTCTGTGCT                                                333
IGRaE11   .T..                                                                                                 102
```

```
Vα2
IGRa09                    AAATCCTTGAGAGTTTTACTAGTGATCCTGTGGCTTCAGCTGAGCCGGGTTTGGAGCCAACAGAAGGAGGTGGAGCA
IGRa09    GAATTCTGGACCCCTCAGTGTTCCAGAGGGAGCCATTGCCTCTCTCAACTGCACTTACAGTGACCGAGGTTCCCAGTCCTTCTTCTGGTACAGACAATAT
IGRaF110
IGRa09    TCTGGGAAAAGCCCTGAGTTGATAATGTCCATATACTCCAATGGTGACAAAGAAGATGGAAGGTTTACAGCACAGCTCAATAAAGCCAGCCAGTATGTTT
IGRaF110
IGRa09    CTCTGCTCATCAGAGACTCCCAGCCCAGTGATTCAGCCACCTACCTCTGTGCC                                                330
IGRaF110                                                                                                        252
```

FIG. 1B

```
Vα5
IGRa10    GGCCACATTTGGGGAGACGAGAATGGAGTCATCCCTGGGAGGTGTTTTGCTGATTTTGTGGCTTCAAGTGGGACTGGGTGAAGAGCAAAAGATAGAACAGAA
HAP35     ..................................................................................................

IGRa10    TTCCGAGGCCCTGAACATTCAGGAGGGTAAAACGGCCACCCTGACCTGCAACTATACACAAACTATTCTCCAGCATACTTACAGTGGTACCGACAAGATCCA
HAP35     ..................................................................................................

IGRa10    GGAAGAGGCCCTGTTTTCTGCTACTCATACGTGAAAATGAGAAAGGAAAAGACTGAAGGTCACCTTTGATACCACCCTTAAACAGAGTT
HAP35     ............................................................................

IGRa10    TGTTTCATATCACAGCCTCCCAGCCTGCAGACTCAGCTACTACCCTCTGTGCT    333
HAP35     ....................................................    249
```

FIG. 1C

```
Vα7
IGRa11    CTCGTGGTATCCTGCAGCAGAATGTGGGGAGTTTTCCTTCTTTATGTTCCATGAAGATGGGAGGCACTACAGGACAAAACATTGACCAGCCCACTGAGAT
HAP12     .................................................................................................

IGRa11    GACAGCTACGGAAGGTGCCATTGTCCAGATCAACTGTGACGTACCAGAGACATCTGGGTTCAACGGGCTGTTCTGGTACCAGCAACATGCTGGCGAAGCACCC
HAP12     ...................................................................................................

IGRa11    ACATTTCTGTCTTACAATGTTCTGGATGGGTTTGGAGGAGAAAGGTCGTTTTTCTTCATTCCTTAGTCGGTCTAAAGGGTACAGTTACCTCCTTTTGAAGG
HAP12     ...................................................................................................

IGRa11    AGCTCCAGATGAAAGACTCTGCCTCTTACCCTCTGTGCT    318
HAP12     .......................................    222
```

FIG. 1D

Vα22  
IGRa12     ATTTGGGTAACACACTAAAGATGAACTATTCTCCAGGCTTAGTAGTATCTTACTGCTTGGAGAACCCGTGGAGATTCAGTGACCCAGATGGA

IGRa12     AGGGCCAGTGACTCTCTCAGAGAGAGGCCTTCCTGACTATAAACTGCACGTACACAGCCACAGGATACCCTTCCCTTTTCTGGTATGTCCAATATCCTGGA

IGRa12     GAAGGTCTACAGCTCCCTGAAAGCCACGAAGGCTGATGACAAGGGAAGCAACAAAAGGTTTTGAAGCCACATACGTAAAGAAACCACTTCTCTTTCCACT
AC9

IGRa12     TGGAGAAAGGCTCAGTTCAAGTGTCAGACTCAGCGGTGTACTTCTCTGCT    330
AC9                                                           113

FIG. 1E

F  G  G  T
IGRJa01G   GGTTATTGCAATAGCACTAAAGACTGTGTAACACCACTAAAGACTGTGTAACACCAGGCAAATCAACCTTTGGGGATGGGACTACGCTCACTGTGAAGCCA
IGRJa02G   GGTTTTTGTAAAAGAATGAGCCATTGTGGATAGGCTTGCTGCTGCACTCAAGTGATTGTTTACCA
IGRJa04                   TAGATACTGGAGGGCTTCAAAACTACTATCTCTTCTTTGGAGCAGGAACAAGACTATTTGTTAAAGCA
IGRJa05                        CCTAACTGGGGCAAGGCCAATAGTAAGCTCTTCATCTTTGGGACTGGAACGACTACCGTTCTTCCC
IGRJa06                             ATGGAGGAAGCCAAGGAATTCTCATCTTTGGAAAATCCACTAAACTCTGTTAAACCA
IGRJa07                                  GGAGCCAATAGTAAGCTGACATTTGGAGTGCTGACCA
IGRJa08                                       CTGGTGGCTACAATAAGCTGATTTTTGGAGCAGGGACCAGGCTGACACCCA
IGRJa09                                            TGGAAACAAGCTGGTCTTCTTTGGCGCAGGAACCATTCAAGTCC

SEQUENCE LISTING ( 1 ) GENERAL INFORMATION:

( i i i ) NUMBER OF SEQUENCES: 62

( 2 ) INFORMATION FOR SEQ ID NO: 1:

( i ) SEQUENCE CHARACTERISTICS:
        ( A ) LENGTH: 371
        ( B ) TYPE: NUCLEOTIDE
        ( C ) STRANDEDNESS: DOUBLE
        ( D ) TOPOLOGY: LINEAR ( i i ) MOLECULE TYPE: cDNA TO mRNA ( v i ) ORIGINAL SOURCE:
        ( A ) ORGANISM: HUMAN
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE: HUMAN T LYMPHOCYTE
        ( I ) ORGANELLE:

( i x ) FEATURE:
        ( A ) NAME/KEY: IGR a O2
        ( B ) LOCATION:
        ( C ) IDENTIFICATION METHOD:
        ( D ) OTHER INFORMATION: SEQUENCE Vα w24

( x i ) SEQUENCE DESCRIPTION: SEQ ID NO:1:

```
AGTCAACTTC TGGGAGCAGT CTCTGCAGAA TAAAA                                    35

ATG AAA AAG CAT CTG ACG ACC TTC TTG GTG ATT TTG                           71
Met Lys Lys His Leu Thr Thr Phe Leu Val Ile Leu
1             5                       10

TGG CTT TAT TTT TAT AGG GGG AAT GGC AAA AAC CAA                           107
Trp Leu Tyr Phe Tyr Arg Gly Asn Gly Lys Asn Gln
        15                  20

GTG GAG CAG AGT CCT CAG TCC CTG ATC ATC CTG GAG                           143
Val Glu Gln Ser Pro Gln Ser Leu Ile Ile Leu Glu
25              30                      35

GGA AAG AAC TGC ACT CTT CAA TGC AAT TAT ACA GTG                           179
Gly Lys Asn Cys Thr Leu Gln Cys Asn Tyr Thr Val
            40              45

AGC CCC TTC AGC AAC TTA AGG TGG TAT AAG CAA GAT                           215
Ser Pro Phe Ser Asn Leu Arg Trp Tyr Lys Gln Asp
    50                  55                  60

ACA ATC ATG ACT TTC AGT GAG AAC ACA AAG TCG AAC                           251
Thr Ile Met Thr Phe Ser Glu Asn Thr Lys Ser Asn
    Gly Arg Gly Pro Val Ser Leu Thr Ile Met Thr
                65                      70

GGA AGA TAT ACA ACT GGG AGA GGT CCT GTT TCC CTG                           287
```

-continued

| | | | | | | | | | | |
|---|---|---|---|---|---|---|---|---|---|---|
| Phe | Ser | Glu | Asn | Thr | Lys | Ser | Asn | Gly | Arg | Tyr | Thr |
| | | 75 | | | | | 80 | | | | |

| GCA | ACT | CTG | GAT | GCA | GAC | ACA | AAG | CAA | AGC | TCT | CTG | 323 |
| Ala | Thr | Leu | Asp | Ala | Asp | Thr | Lys | Gln | Ser | Ser | Leu | |
| 85 | | | | | 90 | | | | | 95 | | |

| CAC | ATC | ACA | GCC | TCC | CAG | CTC | AGC | GAT | TCA | GCC | TCC | 359 |
| His | Ile | Thr | Ala | Ser | Gln | Leu | Ser | Asp | Ser | Ala | Ser | |
| | | | 100 | | | | | 105 | | | | |

| TAC | ATC | TGT | GTG | | | | | | | | | 371 |
| Tyr | Ile | Cys | Val | | | | | | | | | |
| | | 110 | | | | | | | | | | |

( 2 ) INFORMATION FOR SEQ ID NO: 2:

( i ) SEQUENCE CHARACTERISTICS:
        ( A ) LENGTH: 400
        ( B ) TYPE: NUCLEOTIDE
        ( C ) STRANDEDNESS: DOUBLE
        ( D ) TOPOLOGY: LINEAR ( i i ) MOLECULE TYPE: cDNA TO mRNA ( v i ) ORIGINAL SOURCE:
        ( A ) ORGANISM: HUMAN
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE: HUMAN T LYMPHOCYTE
        ( I ) ORGANELLE:

( i x ) FEATURE:
        ( A ) NAME/KEY: IGR a 03
        ( B ) LOCATION:
        ( C ) IDENTIFICATION METHOD:
        ( D ) OTHER INFORMATION: SEQUENCE V α w 25

( x i ) SEQUENCE DESCRIPTION: SEQ ID NO:2:

GACTCTAAGC CCAAGAGAGT TTCTTGAAGC AAAAAAAAA    40

AAAACCCATT CAGGAAATAA TTCTTTGCTG ATAAGG    76

| ATG | CTC | CTT | GAA | CAT | TTA | TTA | ATA | ATC | TTG | TGG | ATG | 112 |
| Met | Leu | Leu | Glu | His | Leu | Leu | Ile | Ile | Leu | Trp | Met | |
| 1 | | | | 5 | | | | | 10 | | | |

| CAG | CTG | ACA | TGG | GTC | AGT | GGT | CAA | CAG | CTG | AAT | CAG | 148 |
| Gln | Leu | Thr | Trp | Val | Ser | Gly | Gln | Gln | Leu | Asn | Gln | |
| | | 15 | | | | | 20 | | | | | |

| AGT | CCT | CAA | TCT | ATG | TTT | ATC | CAG | GAA | GGA | GAA | GAT | 184 |
| Ser | Pro | Gln | Ser | Met | Phe | Ile | Gln | Glu | Gly | Glu | Asp | |
| 25 | | | | | 30 | | | | | 35 | | |

| GTC | TCC | ATG | AAC | TGC | ACT | TCT | TCA | AGC | ATA | TTT | AAC | 220 |
| Val | Ser | Met | Asn | Cys | Thr | Ser | Ser | Ser | Ile | Phe | Asn | |
| | | | 40 | | | | | 45 | | | | |

| ACC | TGG | CTA | TGG | TAC | AAG | CAG | GAC | CCT | GGG | GAA | GGT | 256 |
| Thr | Trp | Leu | Trp | Tyr | Lys | Gln | Asp | Pro | Gly | Glu | Gly | |
| | | 50 | | | | | 55 | | | | 60 | |

| CCT | GTC | CTC | TTG | ATA | GCC | TTA | TAT | AAG | GCT | GGT | GAA | 292 |
| Pro | Val | Leu | Leu | Ile | Ala | Leu | Tyr | Lys | Ala | Gly | Glu | |
| | | | | 65 | | | | | 70 | | | |

| TTG | ACC | TCA | AAT | GGA | AGA | CTG | ACT | GCT | CAG | TTT | GGT | 328 |
| Leu | Thr | Ser | Asn | Gly | Arg | Leu | Thr | Ala | Gln | Phe | Gly | |
| | | 75 | | | | | 80 | | | | | |

| ATA | ACC | AGA | AAG | GAC | AGC | TTC | CTG | AAT | ATC | TCA | GCA | 364 |
| Ile | Thr | Arg | Lys | Asp | Ser | Phe | Leu | Asn | Ile | Ser | Ala | |
| 85 | | | | | 90 | | | | | 95 | | |

```
TCC  ATA  CCT  AGT  GAT  GTA  GGC  ATC  TAC  TTC  TGT  GCT                    400
Ser  Ile  Pro  Ser  Asp  Val  Gly  Ile  Tyr  Phe  Cys  Ala
               100                      105
```

( 2 ) INFORMATION FOR SEQ ID NO: 3:

( i ) SEQUENCE CHARACTERISTICS:
        ( A ) LENGTH: 339
        ( B ) TYPE: NUCLEOTIDE
        ( C ) STRANDEDNESS: DOUBLE
        ( D ) TOPOLOGY: LINEAR ( i i ) MOLECULE TYPE: cDNA to mRNA ( v i ) ORIGINAL SOURCE:
        ( A ) ORGANISM: HUMAN
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE: HUMAN T LYMPHOCYTE
        ( I ) ORGANELLE:

( i x ) FEATURE:
        ( A ) NAME/KEY: IGR a 04
        ( B ) LOCATION:
        ( C ) IDENTIFICATION METHOD:
        ( D ) OTHER INFORMATION: SEQUENCE V α w26

( x i ) SEQUENCE DESCRIPTION: SEQ ID NO:3:

```
AGCTAAGGG  ATG  GAG  ACT  GTT  CTG  CAA  GTA  CTC  CTA                         36
           Met  Glu  Thr  Val  Leu  Gln  Val  Leu  Leu
            1                  5

GGG  ATA  TTG  GGG  TTC  CAA  GCA  GCC  TGG  GTC  AGT  AGC                     72
Gly  Ile  Leu  Gly  Phe  Gln  Ala  Ala  Trp  Val  Ser  Ser
 10                      15                      20

CAA  GAA  CTG  GAG  CAG  AGT  CCT  CAG  TCC  TTG  ATC  GTC                    108
Gln  Glu  Leu  Glu  Gln  Ser  Pro  Gln  Ser  Leu  Ile  Val
               25                      30

CAA  GAG  GGA  AAG  AAT  CTC  ACC  ATA  AAC  TGC  ACG  TCA                    144
Gln  Glu  Gly  Lys  Asn  Leu  Thr  Ile  Asn  Cys  Thr  Ser
      35                       40                       45

TCA  AAG  ACG  TTA  TAT  GGC  TTA  TAC  TGG  TAT  AAG  CAA                    180
Ser  Lys  Thr  Leu  Tyr  Gly  Leu  Tyr  Trp  Tyr  Lys  Gln
                     50                       55

AAG  TAT  GGT  GAA  GGT  CTT  ATC  TTC  TTG  ATG  ATG  CTA                    216
Lys  Tyr  Gly  Glu  Gly  Leu  Ile  Phe  Leu  Met  Met  Leu
           60                      65

CAG  AAA  GGT  GGG  GAA  GAG  AAA  AGT  CAT  GAA  AAG  ATA                    252
Gln  Lys  Gly  Gly  Glu  Glu  Lys  Ser  His  Glu  Lys  Ile
 70                      75                      80

ACT  GCC  AAG  TTG  GAT  GAG  AAA  AAG  CAG  CAA  AGT  TCC                    288
Thr  Ala  Lys  Leu  Asp  Glu  Lys  Lys  Gln  Gln  Ser  Ser
               85                      90

CTG  CAT  ATC  ACA  GCC  TCC  CAG  CCC  AGC  CAT  GCA  GGC                    324
Leu  His  Ile  Thr  Ala  Ser  Gln  Pro  Ser  His  Ala  Gly
      95                      100                     105

ATC  TAC  CTC  TGT  GGA                                                       339
Ile  Tyr  Leu  Cys  Gly
                110
```

( 2 ) INFORMATION FOR SEQ ID NO: 4:

( i ) SEQUENCE CHARACTERISTICS:
        ( A ) LENGTH: 335

( B ) TYPE: NUCLEOTIDE
( C ) STRANDEDNESS: DOUBLE
( D ) TOPOLOGY: LINEAR ( i i ) MOLECULE TYPE: cDNA to mRNA ( v i ) ORIGINAL SOURCE:
( A ) ORGANISM: HUMAN
( B ) STRAIN:
( C ) INDIVIDUAL ISOLATE:
( D ) DEVELOPMENTAL STAGE:
( E ) HAPLOTYPE:
( F ) TISSUE TYPE:
( G ) CELL TYPE:
( H ) CELL LINE: HUMAN T LYMPHOCYTE
( I ) ORGANELLE:

( i x ) FEATURE:
( A ) NAME/KEY: IGR a 05
( B ) LOCATION:
( C ) IDENTIFICATION METHOD:
( D ) OTHER INFORMATION: SEQUENCE V α w27

( x i ) SEQUENCE DESCRIPTION: SEQ ID NO:4:

```
AGAAAAAAAA  AATGAAGAAG  CTACTAGCAA  TGATCCTGTG                    40

GCTTCAACTA  GACCGGTTAA  GTGGAGAGCT  GAAAGTG                       77

GAA  CAA  AAC  CCT  CTG  TTC  CTG  AGC  ATG  CAG  GAG  GGA       113
Glu  Gln  Asn  Pro  Leu  Phe  Leu  Ser  Met  Gln  Glu  Gly
1                   5                        10

AAA  AAC  TAT  ACC  ATC  TAC  TGC  AAT  TAT  TCA  ACC  ACT       149
Lys  Asn  Tyr  Thr  Ile  Tyr  Cys  Asn  Tyr  Ser  Thr  Thr
          15                       20

TCA  GAC  AGA  CTG  TAT  TGG  TAC  AGG  CAG  GAT  CCT  GGG       185
Ser  Asp  Arg  Leu  Tyr  Trp  Tyr  Arg  Gln  Asp  Pro  Gly
25                       30                        35

AAA  AGT  CTG  GAA  TCT  CTG  TTT  GTG  TTG  CTA  TCA  AAT       221
Lys  Ser  Leu  Glu  Ser  Leu  Phe  Val  Leu  Leu  Ser  Asn
               40                       45

GGA  GCA  GTG  AAG  CAG  GAG  GGA  CGA  TTA  ATG  GCC  TCA       257
Gly  Ala  Val  Lys  Gln  Glu  Gly  Arg  Leu  Met  Ala  Ser
          50                       55                  60

CTT  GAT  ACC  AAA  GCC  CGT  CTC  AGC  ACC  CTC  CAC  ATC       293
Leu  Asp  Thr  Lys  Ala  Arg  Leu  Ser  Thr  Leu  His  Ile
                    65                       70

ACA  GCT  GCC  GTG  CAT  GAC  CTC  TCT  GCC  ACC  TAC  TTC       329
Thr  Ala  Ala  Val  His  Asp  Leu  Ser  Ala  Thr  Tyr  Phe
               75                       80

TGT  GCC                                                          335
Cys  Ala
85
```

( 2 ) INFORMATION FOR SEQ ID NO: 5:

( i ) SEQUENCE CHARACTERISTICS:
( A ) LENGTH: 361
( B ) TYPE: NUCLEOTIDE
( C ) STRANDEDNESS: DOUBLE
( D ) TOPOLOGY: LINEAR ( i i ) MOLECULE TYPE: cDNA to mRNA ( v i ) ORIGINAL SOURCE:
( A ) ORGANISM: HUMAN
( B ) STRAIN:
( C ) INDIVIDUAL ISOLATE:
( D ) DEVELOPMENTAL STAGE:
( E ) HAPLOTYPE:
( F ) TISSUE TYPE:
( G ) CELL TYPE:

-continued (H) CELL LINE: HUMAN T LYMPHOCYTE
(I) ORGANELLE:

(ix) FEATURE:
(A) NAME/KEY: IGR a 07
(B) LOCATION:
(C) IDENTIFICATION METHOD:
(D) OTHER INFORMATION: SEQUENCE V α w29

(xi) SEQUENCE DESCRIPTION: SEQ ID NO:5:

| GAAGCTGACT | GGATATTCTG | GCAGGCCAAG | G | ATG | GAG | ACT | | | | | 40 |
|---|---|---|---|---|---|---|---|---|---|---|---|
| | | | | Met | Glu | Thr | | | | | |
| | | | | 1 | | | | | | | |
| CTC | CTG | AAA | GTG | CCT | TCA | GGC | ACC | TTG | TTG | TGG CAG | 76 |
| Leu | Leu | Lys | Val | Pro | Ser | Gly | Thr | Leu | Leu | Trp Gln | |
| | | 5 | | | | | 10 | | | | |
| TTG | ACC | TGG | GTG | GGA | AGC | CAA | CAA | CCA | GTG | CAG AGT | 112 |
| Leu | Thr | Trp | Val | Gly | Ser | Gln | Gln | Pro | Val | Gln Ser | |
| 15 | | | | | 20 | | | | | 25 | |
| CCT | CAA | GCC | GTG | ATC | CTC | CGA | GAA | GGG | GAA | GAT GCT | 148 |
| Pro | Gln | Ala | Val | Ile | Leu | Arg | Glu | Gly | Glu | Asp Ala | |
| | | | | 30 | | | | 35 | | | |
| GTC | ACC | AAC | TGC | AGT | TCC | TCC | AAG | GCT | TTA | TAT TCT | 184 |
| Val | Thr | Asn | Cys | Ser | Ser | Ser | Lys | Ala | Leu | Tyr Ser | |
| | 40 | | | | | 45 | | | | 50 | |
| GTA | CAC | TGG | TAC | AGG | CAG | AAG | CAT | GGT | GAA | GCA CCC | 220 |
| Val | His | Trp | Tyr | Arg | Gln | Lys | His | Gly | Glu | Ala Pro | |
| | | | | 55 | | | | | 60 | | |
| GTC | TTC | CTG | ATG | ATA | TTA | CTG | AAG | GGT | GGA | GAA CAG | 256 |
| Val | Phe | Leu | Met | Ile | Leu | Leu | Lys | Gly | Gly | Glu Gln | |
| | | 65 | | | | | 70 | | | | |
| ATG | CGT | CGT | GAA | AAA | ATA | TCT | GCT | TCA | TTT | AAT GAA | 292 |
| Met | Arg | Arg | Glu | Lys | Ile | Ser | Ala | Ser | Phe | Asn Glu | |
| 75 | | | | | 80 | | | | | 85 | |
| AAA | AAG | CAG | CAA | AGC | TCC | CTG | TAC | CTT | ACG | GCC TCC | 328 |
| Lys | Lys | Gln | Gln | Ser | Ser | Leu | Tyr | Leu | Thr | Ala Ser | |
| | | | 90 | | | | | 95 | | | |
| CAG | CTC | AGT | TAC | TCA | GGA | ACC | TAC | TTC | TGC | GGG | 361 |
| Gln | Leu | Ser | Tyr | Ser | Gly | Thr | Tyr | Phe | Cys | Gly | |
| | | 100 | | | | | 105 | | | | |

(2) INFORMATION FOR SEQ ID NO: 6:

(i) SEQUENCE CHARACTERISTICS:
(A) LENGTH: 569
(B) TYPE: NUCLEOTIDE
(C) STRANDEDNESS: DOUBLE
(D) TOPOLOGY: LINEAR (ii) MOLECULE TYPE: cDNA to mRNA (vi) ORIGINAL SOURCE:
(A) ORGANISM: HUMAN
(B) STRAIN:
(C) INDIVIDUAL ISOLATE:
(D) DEVELOPMENTAL STAGE:
(E) HAPLOTYPE:
(F) TISSUE TYPE:
(G) CELL TYPE:
(H) CELL LINE: HUMAN T LYMPHOCYTE
(I) ORGANELLE:

(ix) FEATURE:
(A) NAME/KEY: IGR a 08
(B) LOCATION:
(C) IDENTIFICATION METHOD:
(D) OTHER INFORMATION: SEQUENCE V α 1

(xi) SEQUENCE DESCRIPTION: SEQ ID NO:6:

```
TCAGTTTCTT  CTTCCTGCAG  CTGGTTGAGT  TCTTTCCAGA                              40

CAAAGACAAG  TGACAAGAAT  TAGAGGTTTA  AAAAGCAACC                              80

AGATTCATCT  CAGCAGCTTT  TGTAGTTTTA  AATAAGCAAG                             120

GAGTTTCTCC  AGCGAAACTT  CCTCACACCT  CTTGGTCTTG                             160

GTCTCTTCAG  ACACTTTCCT  TCCTGTTCTC  TGGAGATCTT                             200

GCAGAAAAGA  GCCTGCAGTG  TTTCCCTTGC  TCAGCC  ATG                            239
                                            Met
                                             1

CTC  CTG  GAG  CTT  ATC  CCA  CTG  CTG  GGG  ATA  CAT  TTT                 275
Leu  Leu  Glu  Leu  Ile  Pro  Leu  Leu  Gly  Ile  His  Phe
               5                        10

GTC  CTG  AGA  ACT  GCC  AGA  GCC  CAG  TCA  GTG  ACC  CAG                 311
Val  Leu  Arg  Thr  Ala  Arg  Ala  Gln  Ser  Val  Thr  Gln
     15                   20                         25

CCT  GAC  ATC  CAC  ATC  ACT  GTC  TCT  GAA  GGA  GCC  TCA                 347
Pro  Asp  Ile  His  Ile  Thr  Val  Ser  Glu  Gly  Ala  Ser
                    30                        35

CTG  GAG  TTG  AGA  TGT  AAC  TAT  TCC  TAT  GGG  GCA  ACA                 383
Leu  Glu  Leu  Arg  Cys  Asn  Tyr  Ser  Tyr  Gly  Ala  Thr
          40                        45

CCT  TAT  CTC  TTC  TGG  TAT  GTC  CAG  TCC  CCC  GGC  CAA                 419
Pro  Tyr  Leu  Phe  Trp  Tyr  Val  Gln  Ser  Pro  Gly  Gln
50                        55                        60

GGC  CTC  CAG  CTG  CTC  CTG  AAG  TAC  TTT  TCA  GGA  GAC                 455
Gly  Leu  Gln  Leu  Leu  Leu  Lys  Tyr  Phe  Ser  Gly  Asp
               65                        70

ACT  CTG  GTT  CAA  GGC  ATT  AAA  GGC  TTT  GAG  GCT  GAA                 491
Thr  Leu  Val  Gln  Gly  Ile  Lys  Gly  Phe  Glu  Ala  Glu
     75                   80                         85

TTT  AAG  AGG  AGT  CAA  TCT  TCC  TTC  AAC  CTG  AGG  AAA                 527
Phe  Lys  Arg  Ser  Gln  Ser  Ser  Phe  Asn  Leu  Arg  Lys
                    90                        95

CCC  TCT  GTG  CAT  TGG  AGT  GAT  GCT  GCT  GAG  TAC  TTC                 563
Pro  Ser  Val  His  Trp  Ser  Asp  Ala  Ala  Glu  Tyr  Phe
               100                       105

TGT  GCT                                                                   569
Cys  Ala
110
```

( 2 ) INFORMATION FOR SEQ ID NO: 7:

( i ) SEQUENCE CHARACTERISTICS:
        ( A ) LENGTH: 330
        ( B ) TYPE: NUCLEOTIDE
        ( C ) STRANDEDNESS: DOUBLE
        ( D ) TOPOLOGY: LINEAR ( i i ) MOLECULE TYPE: cDNA to mRNA ( v i ) ORIGINAL SOURCE:
        ( A ) ORGANISM: HUMAN
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE: HUMAN T LYMPHOCYTE
        ( I ) ORGANELLE:

( i x ) FEATURE:
        ( A ) NAME/KEY: IGR a 09
        ( B ) LOCATION:

(C) IDENTIFICATION METHOD:
(D) OTHER INFORMATION: SEQUENCE V α 2

(xi) SEQUENCE DESCRIPTION: SEQ ID NO:7:

```
AAA  TCC  TTG  AGA  GTT  TTA  CTA  GTG  ATC  CTG  TGG  CTT                36
Lys  Ser  Leu  Arg  Val  Leu  Leu  Val  Ile  Leu  Trp  Leu
1              5                             10

CAG  CTG  AGC  CGG  GTT  TGG  AGC  CAA  CAG  AAG  GAG  GTG                72
Gln  Leu  Ser  Arg  Val  Trp  Ser  Gln  Gln  Lys  Glu  Val
               15                            20

GAG  CAG  AAT  TCT  GGA  CCC  CTC  AGT  GTT  CCA  GAG  GGA               108
Glu  Gln  Asn  Ser  Gly  Pro  Leu  Ser  Val  Pro  Glu  Gly
25                       30                            35

GCC  ATT  GCC  TCT  CTC  AAC  TGC  ACT  TAC  AGT  GAC  CGA               144
Ala  Ile  Ala  Ser  Leu  Asn  Cys  Thr  Tyr  Ser  Asp  Arg
                    40                   45

GGT  TCC  CAG  TCC  TTC  TTC  TGG  TAC  AGA  CAA  TAT  TCT               180
Gly  Ser  Gln  Ser  Phe  Phe  Trp  Tyr  Arg  Gln  Tyr  Ser
     50                        55                           60

GGG  AAA  AGC  CCT  GAG  TTG  ATA  ATG  TCC  ATA  TAC  TCC               216
Gly  Lys  Ser  Pro  Glu  Leu  Ile  Met  Ser  Ile  Tyr  Ser
                    65                        70

AAT  GGT  GAC  AAA  GAA  GAT  GGA  AGG  TTT  ACA  GCA  CAG               252
Asn  Gly  Asp  Lys  Glu  Asp  Gly  Arg  Phe  Thr  Ala  Gln
          75                        80

CTC  AAT  AAA  GCC  AGC  CAG  TAT  GTT  TCT  CTG  CTC  ATC               288
Leu  Asn  Lys  Ala  Ser  Gln  Tyr  Val  Ser  Leu  Leu  Ile
85                       90                            95

AGA  GAC  TCC  CAG  CCC  AGT  GAT  TCA  GCC  ACC  TAC  CTC               324
Arg  Asp  Ser  Gln  Pro  Ser  Asp  Ser  Ala  Thr  Tyr  Leu
               100                       105

TGT  GCC                                                                  330
Cys  Ala
110
```

(2) INFORMATION FOR SEQ ID NO: 8:

(i) SEQUENCE CHARACTERISTICS:
        (A) LENGTH: 400
        (B) TYPE: NUCLEOTIDE
        (C) STRANDEDNESS: DOUBLE
        (D) TOPOLOGY: LINEAR (ii) MOLECULE TYPE: cDNA to mRNA (vi) ORIGINAL SOURCE:
        (A) ORGANISM: HUMAN
        (B) STRAIN:
        (C) INDIVIDUAL ISOLATE:
        (D) DEVELOPMENTAL STAGE:
        (E) HAPLOTYPE:
        (F) TISSUE TYPE:
        (G) CELL TYPE:
        (H) CELL LINE: HUMAN T LYMPHOCYTE
        (I) ORGANELLE:

(ix) FEATURE:
        (A) NAME/KEY: IGR a 10
        (B) LOCATION:
        (C) IDENTIFICATION METHOD:
        (D) OTHER INFORMATION: SEQUENCE V α 5

(xi) SEQUENCE DESCRIPTION: SEQ ID NO:8:

```
GCCAAACAGA  ATGGCTTTTT  GGCTGAGAAG  GCTGGGTCTA                             40

CATTTCAGGC  CACATTTGGG  GAGACGA  ATG  GAG  TCA                             76
                                Met  Glu  Ser
                                1
```

| | | | | | | | | | | |
|---|---|---|---|---|---|---|---|---|---|---|
| TCC | CTG | GGA | GGT | GTT | TTG | CTG | ATT | TTG | TGG | CTT | CAA | 112 |
| Ser | Leu | Gly | Gly | Val | Leu | Leu | Ile | Leu | Trp | Leu | Gln | |
| | 5 | | | | 10 | | | | | 15 | | |
| GTG | GAC | TGG | GTG | AAG | AGC | CAA | AAG | ATA | GAA | CAG | AAT | 148 |
| Val | Asp | Trp | Val | Lys | Ser | Gln | Lys | Ile | Glu | Gln | Asn | |
| | | | 20 | | | | | 25 | | | | |
| TCC | GAG | GCC | CTG | AAC | ATT | CAG | GAG | GGT | AAA | ACG | GCC | 184 |
| Ser | Glu | Ala | Leu | Asn | Ile | Gln | Glu | Gly | Lys | Thr | Ala | |
| | | 30 | | | | | 35 | | | | | |
| ACC | CTG | ACC | TGC | AAC | TAT | ACA | AAC | TAT | TCT | CCA | GCA | 220 |
| Thr | Leu | Thr | Cys | Asn | Tyr | Thr | Asn | Tyr | Ser | Pro | Ala | |
| 40 | | | | 45 | | | | | 50 | | | |
| TAC | TTA | CAG | TGG | TAC | CGA | CAA | GAT | CCA | GGA | AGA | GGC | 256 |
| Tyr | Leu | Gln | Trp | Tyr | Arg | Gln | Asp | Pro | Gly | Arg | Gly | |
| | | | 55 | | | | | 60 | | | | |
| CCT | GTT | TTC | TTG | CTA | CTC | ATA | CGT | GAA | AAT | GAG | AAA | 292 |
| Pro | Val | Phe | Leu | Leu | Leu | Ile | Arg | Glu | Asn | Glu | Lys | |
| | 65 | | | | 70 | | | | | 75 | | |
| GAA | AAA | AGG | AAA | GAA | AGA | CTG | AAG | GTC | ACC | TTT | GAT | 328 |
| Glu | Lys | Arg | Lys | Glu | Arg | Leu | Lys | Val | Thr | Phe | Asp | |
| | | | | 80 | | | | 85 | | | | |
| ACC | ACC | CTT | AAA | CAG | AGT | TTG | TTT | CAT | ATC | ACA | GCC | 364 |
| Thr | Thr | Leu | Lys | Gln | Ser | Leu | Phe | His | Ile | Thr | Ala | |
| | | 90 | | | | 95 | | | | | | |
| TCC | CAG | CCT | GCA | GAC | TCA | GCT | ACC | TAC | CTC | TGT | GCT | 400 |
| Ser | Gln | Pro | Ala | Asp | Ser | Ala | Thr | Tyr | Leu | Cys | Ala | |
| 100 | | | | | 105 | | | | | 110 | | |

( 2 ) INFORMATION FOR SEQ ID NO: 9:

( i ) SEQUENCE CHARACTERISTICS:
        ( A ) LENGTH: 386
        ( B ) TYPE: NUCLEOTIDE
        ( C ) STRANDEDNESS: DOUBLE
        ( D ) TOPOLOGY: LINEAR ( i i ) MOLECULE TYPE: cDNA to mRNA ( v i ) ORIGINAL SOURCE:
        ( A ) ORGANISM: HUMAN
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE: HUMAN T LYMPHOCYTE
        ( I ) ORGANELLE:

( i x ) FEATURE:
        ( A ) NAME/KEY: IGR a 11
        ( B ) LOCATION:
        ( C ) IDENTIFICATION METHOD:
        ( D ) OTHER INFORMATION: SEQUENCE V α 7

( x i ) SEQUENCE DESCRIPTION: SEQ ID NO:9:

| | | |
|---|---|---|
| GCCTTCTGCA GACTCCAATG GCTCAGGAAC TGGGAATGCA | | 40 |
| GTGCCAGGCT CGTGGTATCC TGCAGCAG ATG TGG GGA | | 77 |
|                                                  Met Trp Gly | | |
|                                                     1 | | |

| | | | | | | | | | | | |
|---|---|---|---|---|---|---|---|---|---|---|---|
| GTT | TTC | CTT | CTT | TAT | GTT | TCC | ATG | AAG | ATG | GGA | GGC | 113 |
| Val | Phe | Leu | Leu | Tyr | Val | Ser | Met | Lys | Met | Gly | Gly | |
| | 5 | | | | 10 | | | | | 15 | | |
| ACT | ACA | GGA | CAA | AAC | ATT | GAC | CAG | CCC | ACT | GAG | ATG | 149 |
| Thr | Thr | Gly | Gln | Asn | Ile | Asp | Gln | Pro | Thr | Glu | Met | |
| | | | 20 | | | | | 25 | | | | |

```
ACA GCT ACG GAA GGT GCC ATT GTC CAG ATC AAC TGC          185
Thr Ala Thr Glu Gly Ala Ile Val Gln Ile Asn Cys
    30                      35

ACG TAC CAG ACA TCT GGG TTC AAC GGG CTG TTC TGG          221
Thr Tyr Gln Thr Ser Gly Phe Asn Gly Leu Phe Trp
40              45                      50

TAC CAG CAA CAT GCT GGC GAA GCA CCC ACA TTT CTG          257
Tyr Gln Gln His Ala Gly Glu Ala Pro Thr Phe Leu
        55                      60

TCT TAC AAT GTT CTG GAT GGT TTG GAG GAG AAA GGT          293
Ser Tyr Asn Val Leu Asp Gly Leu Glu Glu Lys Gly
    65                  70                  75

CGT TTT TCT TCA TTC CTT AGT CGG TCT AAA GGG TAC          329
Arg Phe Ser Ser Phe Leu Ser Arg Ser Lys Gly Tyr
                80                  85

AGT TAC CTC CTT TTG AAG GAG CTC CAG ATG AAA GAC          365
Ser Tyr Leu Leu Leu Lys Glu Leu Gln Met Lys Asp
        90                  95

TCT GCC TCT TAC CTC TGT GCT                              386
Ser Ala Ser Tyr Leu Cys Ala
100             105
```

( 2 ) INFORMATION FOR SEQ ID NO: 10:

( i ) SEQUENCE CHARACTERISTICS:
    ( A ) LENGTH: 383
    ( B ) TYPE: NUCLEOTIDE
    ( C ) STRANDEDNESS: DOUBLE
    ( D ) TOPOLOGY: LINEAR ( i i ) MOLECULE TYPE: cDNA TO mRNA ( v i ) ORIGINAL SOURCE:
    ( A ) ORGANISM: HUMAN
    ( B ) STRAIN:
    ( C ) INDIVIDUAL ISOLATE:
    ( D ) DEVELOPMENTAL STAGE:
    ( E ) HAPLOTYPE:
    ( F ) TISSUE TYPE:
    ( G ) CELL TYPE:
    ( H ) CELL LINE: HUMAN T LYMPHOCYTE
    ( I ) ORGANELLE:

( i x ) FEATURE:
    ( A ) NAME/KEY: IGR a 12
    ( B ) LOCATION:
    ( C ) IDENTIFICATION METHOD:
    ( D ) OTHER INFORMATION: SEQUENCE V α 22

( x i ) SEQUENCE DESCRIPTION: SEQ ID NO:10:

```
TGTGACTTCT TCATGTTAAG GATCAAGACC ATTATTTGGG              40

TAACACACTA AAG ATG AAC TAT TCT CCA GGC TTA               74
            Met Asn Tyr Ser Pro Gly Leu
            1               5

GTA TCT CTG ATA CTC TTA CTG CTT GGA AGA ACC CGT          110
Val Ser Leu Ile Leu Leu Leu Leu Gly Arg Thr Arg
        10                  15

GGA GAT TCA GTG ACC CAG ATG GAA GGG CCA GTG ACT          146
Gly Asp Ser Val Thr Gln Met Glu Gly Pro Val Thr
20              25                      30

CTC TCA GAA GAG GCC TTC CTG ACT ATA AAC TGC ACG          182
Leu Ser Glu Glu Ala Phe Leu Thr Ile Asn Cys Thr
        35                      40

TAC ACA GCC ACA GGA TAC CCT TCC CTT TTC TGG TAT          218
Tyr Thr Ala Thr Gly Tyr Pro Ser Leu Phe Trp Tyr
    45                  50                  55
```

-continued

```
GTC CAA TAT CCT GGA GAA GGT CTA CAG CTC CTC CTG                          254
Val Gln Tyr Pro Gly Glu Gly Leu Gln Leu Leu Leu
             60                  65

AAA GCC ACG AAG GCT GAT GAC AAG GGA AGC AAC AAA                          290
Lys Ala Thr Lys Ala Asp Asp Lys Gly Ser Asn Lys
         70                  75

GGT TTT GAA GCC ACA TAC CGT AAA GAA ACC ACT TCT                          326
Gly Phe Glu Ala Thr Tyr Arg Lys Glu Thr Thr Ser
 80                  85                  90

TTC CAC TTG GAG AAA GGC TCA GTT CAA GTG TCA GAC                          362
Phe His Leu Glu Lys Gly Ser Val Gln Val Ser Asp
             95                  100

TCA GCG GTG TAC TTC TGT GCT                                              383
Ser Ala Val Tyr Phe Cys Ala
         105                 110
```

( 2 ) INFORMATION FOR SEQ ID NO: 11:

( i ) SEQUENCE CHARACTERISTICS:
        ( A ) LENGTH: 364
        ( B ) TYPE: NUCLEOTIDE
        ( C ) STRANDEDNESS: DOUBLE
        ( D ) TOPOLOGY: LINEAR ( i i ) MOLECULE TYPE: cDNA to mRNA ( v i ) ORIGINAL SOURCE:
        ( A ) ORGANISM: HUMAN
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE: HUMAN T LYMPHOCYTE
        ( I ) ORGANELLE:

( i x ) FEATURE:
        ( A ) NAME/KEY: IGR α 13
        ( B ) LOCATION:
        ( C ) IDENTIFICATION METHOD:
        ( D ) OTHER INFORMATION: SEQUENCE V α 16

( x i ) SEQUENCE DESCRIPTION: SEQ ID NO:11:

```
AATCCCGCCC GCCGTGAGCT TAGCTGGAGC C ATG GCC TCT                            40
                                  Met Ala Ser
                                   1

GCA CCC ATC TCG ATG CTT GCG ATG CTC TTC ACA TTG                           76
Ala Pro Ile Ser Met Leu Ala Met Leu Phe Thr Leu
         5                  10                  15

AGT GGG CTG AGA GCT CAG TCA GTG GCT CAG CCG GAA                          112
Ser Gly Leu Arg Ala Gln Ser Val Ala Gln Pro Glu
             20                  25

GAT CAG GTC AAC GTT GCT GAA GGG AAT CCT CTG ACT                          148
Asp Gln Val Asn Val Ala Glu Gly Asn Pro Leu Thr
         30                  35

GTG AAA TGC ACC TAT TCA GTC TCT GGA AAC CCT TAT                          184
Val Lys Cys Thr Tyr Ser Val Ser Gly Asn Pro Tyr
 40                  45                  50

CTT TTT TGG TAT GTT CAA TAC CCC AAC CGA GGC CTC                          220
Leu Phe Trp Tyr Val Gln Tyr Pro Asn Arg Gly Leu
             55                  60

CAG TTC CTT CTG AAA TAC ATC ACA GGG GAT AAC CTG                          256
Gln Phe Leu Leu Lys Tyr Ile Thr Gly Asp Asn Leu
 65                  70                  75

GTT AAA GGC AGC TAT GGC TTT GAA GCT GAA TTT AAC                          292
```

|   |   |   |   |   |   |   |   |   |   |   |
|---|---|---|---|---|---|---|---|---|---|---|
| Val | Lys | Gly | Ser | Tyr | Gly | Phe | Glu | Ala | Glu | Phe | Asn |
|   |   |   |   | 80 |   |   |   | 85 |   |   |   |

| AAG | AGC | CAA | ACC | TCC | TTC | CAC | CTG | AAG | AAA | CCA | TCT | 328 |
|---|---|---|---|---|---|---|---|---|---|---|---|---|
| Lys | Ser | Gln | Thr | Ser | Phe | His | Leu | Lys | Lys | Pro | Ser |   |
|   |   | 90 |   |   |   |   | 95 |   |   |   |   |   |

| GCC | CTT | GTG | AGC | GAC | TCC | GCT | TTG | TAC | TTC | TGT | GCT | 364 |
|---|---|---|---|---|---|---|---|---|---|---|---|---|
| Ala | Leu | Val | Ser | Asp | Ser | Ala | Leu | Tyr | Phe | Cys | Ala |   |
| 100 |   |   |   |   | 105 |   |   |   |   | 110 |   |   |

( 2 ) INFORMATION FOR SEQ ID NO: 12:

( i ) SEQUENCE CHARACTERISTICS:
        ( A ) LENGTH: 263
        ( B ) TYPE: NUCLEOTIDE
        ( C ) STRANDEDNESS: DOUBLE
        ( D ) TOPOLOGY: LINEAR ( i i ) MOLECULE TYPE: cDNA to mRNA ( v i ) ORIGINAL SOURCE:
        ( A ) ORGANISM: HUMAN
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE: HUMAN T LYMPHOCYTE
        ( I ) ORGANELLE:

( i x ) FEATURE:
        ( A ) NAME/KEY: Jα 01
        ( B ) LOCATION:
        ( C ) IDENTIFICATION METHOD:
        ( D ) OTHER INFORMATION: SEQUENCE Jα60

( x i ) SEQUENCE DESCRIPTION: SEQ ID NO:12:

| CCTTCAAGGA | AAATTAAGGC | AAATAGAATT | GGGCTGGGGA | 40 |
|---|---|---|---|---|
| GTTGCTACTT | ATTAGTATTC | CTCCCACGTT | CTAACCTAAT | 80 |
| TATAAGGAGG | TTGTTTTGGC | CATGGGCAGT | CATCTCAGGT | 120 |
| TTTGTTTTCC | TGCTTTCCTC | CCTAACCTCC | ACCTGTCTTC | 160 |
| CTAGAGGCCT | GAGTCAAGGT | TATTGCAATA | GCACTAAAGA | 200 |

| CTGTGT | AAC | ACC | AAT | GCA | GGC | AAA | TCA | ACC | TTT | 233 |
|---|---|---|---|---|---|---|---|---|---|---|
|   | Asn | Thr | Asn | Ala | Gly | Lys | Ser | Thr | Phe |   |
|   | 1 |   |   | 5 |   |   |   |   |   |   |

| GGG | GAT | GGG | ACT | ACG | CTC | ACT | GTG | AAG | CCA | 263 |
|---|---|---|---|---|---|---|---|---|---|---|
| Gly | Asp | Gly | Thr | Thr | Leu | Thr | Val | Lys | Pro |   |
| 10 |   |   |   |   | 15 |   |   |   |   |   |

( 2 ) INFORMATION FOR SEQ ID NO: 13:

( i ) SEQUENCE CHARACTERISTICS:
        ( A ) LENGTH: 277
        ( B ) TYPE: NUCLEOTIDE
        ( C ) STRANDEDNESS: DOUBLE
        ( D ) TOPOLOGY: LINEAR ( i i ) MOLECULE TYPE: cDNA to mRNA ( v i ) ORIGINAL SOURCE:
        ( A ) ORGANISM: HUMAN
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE: HUMAN T LYMPHOCYTE
        ( I ) ORGANELLE:

( i x ) FEATURE:
  ( A ) NAME/KEY: Jα 02
  ( B ) LOCATION:
  ( C ) IDENTIFICATION METHOD:
  ( D ) OTHER INFORMATION: SEQUENCE Jα60

( x i ) SEQUENCE DESCRIPTION: SEQ ID NO:13:

```
AAGGACACAG  ACTGCCTGCA  TGAAGGCTGG  AGCTGGGCCC                         40

AGGATGAGGA  AAGGCCTCAG  GAAGGAAGGG  CTGACACGAA                         80

ATAAGGAATA  CCATGGCATT  CATGAGATGT  GCGTCTGAAT                        120

CCTCTCTCTT  GCCTGAGAAG  CTTTAGCTTC  CACCTTGAGA                        160

CACAAAACAT  GTGGTTATGA  AGAGATGACA  AGGTTTTTGT                        200

AAAAGAATGA  GCCATTGTGG  ATA  GGC  TTT  GGG  AAT                       235
                          Ile  Gly  Phe  Gly  Asn
                           1                  5

GTG  CTG  CAT  TGC  GGG  TCC  GGC  ACT  CAA  GTG  ATT  GTT            271
Val  Leu  His  Cys  Gly  Ser  Gly  Thr  Gln  Val  Ile  Val
               10                         15

TTA  CCA                                                              277
Leu  Pro
```

( 2 ) INFORMATION FOR SEQ ID NO: 14:

( i ) SEQUENCE CHARACTERISTICS:
    ( A ) LENGTH: 60
    ( B ) TYPE: NUCLEOTIDE
    ( C ) STRANDEDNESS: DOUBLE
    ( D ) TOPOLOGY: LINEAR ( i i ) MOLECULE TYPE: cDNA to mRNA ( v i ) ORIGINAL SOURCE:
    ( A ) ORGANISM: HUMAN
    ( B ) STRAIN:
    ( C ) INDIVIDUAL ISOLATE:
    ( D ) DEVELOPMENTAL STAGE:
    ( E ) HAPLOTYPE:
    ( F ) TISSUE TYPE:
    ( G ) CELL TYPE:
    ( H ) CELL LINE: HUMAN T LYMPHOCYTE
    ( I ) ORGANELLE:

( i x ) FEATURE:
    ( A ) NAME/KEY: Jα 04
    ( B ) LOCATION:
    ( C ) IDENTIFICATION METHOD:
    ( D ) OTHER INFORMATION: SEQUENCE Jα60

( x i ) SEQUENCE DESCRIPTION: SEQ ID NO:14:

```
TA  GAT  ACT  GGA  GGC  TTC  AAA  ACT  ATC  TTT  GGA  GCA             35
    Asp  Thr  Gly  Gly  Phe  Lys  Thr  Ile  Phe  Gly  Ala
    1              5                        10

GGA  ACA  AGA  CTA  TTT  GTT  AAA  GCA  A                             60
Gly  Thr  Arg  Leu  Phe  Val  Lys  Ala
               15
```

( 2 ) INFORMATION FOR SEQ ID NO: 15:

( i ) SEQUENCE CHARACTERISTICS:
    ( A ) LENGTH: 59
    ( B ) TYPE: NUCLEOTIDE
    ( C ) STRANDEDNESS: DOUBLE
    ( D ) TOPOLOGY: LINEAR ( i i ) MOLECULE TYPE: cDNA to mRNA ( v i ) ORIGINAL SOURCE:

5,798,231

37

-continued ( A ) ORGANISM: HUMAN
             ( B ) STRAIN:
             ( C ) INDIVIDUAL ISOLATE:
             ( D ) DEVELOPMENTAL STAGE:
             ( E ) HAPLOTYPE:
             ( F ) TISSUE TYPE:
             ( G ) CELL TYPE:
             ( H ) CELL LINE: HUMAN T LYMPHOCYTE
             ( I ) ORGANELLE:

( i x ) FEATURE:
             ( A ) NAME/KEY: Ja 05
             ( B ) LOCATION:
             ( C ) IDENTIFICATION METHOD:
             ( D ) OTHER INFORMATION: SEQUENCE Jα60

( x i ) SEQUENCE DESCRIPTION: SEQ ID NO:15:

```
C CTA ACT GGG GCA AAC AAC GTC TTC TTT GGG ACT                    34
  Leu Thr Gly Ala Asn Asn Val Phe Phe Gly Thr
  1               5                   10

GGA ACG AGA CTC ACC GTT CTT CCC T                                59
Gly Thr Arg Leu Thr Val Leu Pro
                15
```

( 2 ) INFORMATION FOR SEQ ID NO: 16:

( i ) SEQUENCE CHARACTERISTICS:
             ( A ) LENGTH: 60
             ( B ) TYPE: NUCLEOTIDE
             ( C ) STRANDEDNESS: DOUBLE
             ( D ) TOPOLOGY: LINEAR ( i i ) MOLECULE TYPE: cDNA to mRNA ( v i ) ORIGINAL SOURCE:
             ( A ) ORGANISM: HUMAN
             ( B ) STRAIN:
             ( C ) INDIVIDUAL ISOLATE:
             ( D ) DEVELOPMENTAL STAGE:
             ( E ) HAPLOTYPE:
             ( F ) TISSUE TYPE:
             ( G ) CELL TYPE:
             ( H ) CELL LINE: HUMAN T LYMPHOCYTE
             ( I ) ORGANELLE:

( i x ) FEATURE:
             ( A ) NAME/KEY: Ja 06
             ( B ) LOCATION:
             ( C ) IDENTIFICATION METHOD:
             ( D ) OTHER INFORMATION: SEQUENCE Jα60

( x i ) SEQUENCE DESCRIPTION: SEQ ID NO: 16:

```
AT GGA GGA AGC CAA GGA AAT CTC ATC TTT GGA AAA                   35
   Gly Gly Ser Gln Gly Asn Leu Ile Phe Gly Lys
   1               5                   10

GGC ACT AAA CTC TCT GTT AAA CCA A                                60
Gly Thr Lys Leu Ser Val Lys Pro
                15
```

( 2 ) INFORMATION FOR SEQ ID NO: 17:

( i ) SEQUENCE CHARACTERISTICS:
             ( A ) LENGTH: 56
             ( B ) TYPE: NUCLEOTIDE
             ( C ) STRANDEDNESS: DOUBLE
             ( D ) TOPOLOGY: LINEAR ( i i ) MOLECULE TYPE: cDNA to mRNA ( v i ) ORIGINAL SOURCE:
             ( A ) ORGANISM: HUMAN
             ( B ) STRAIN:
             ( C ) INDIVIDUAL ISOLATE:
             ( D ) DEVELOPMENTAL STAGE:

( E ) HAPLOTYPE:
            ( F ) TISSUE TYPE:
            ( G ) CELL TYPE:
            ( H ) CELL LINE: HUMAN T LYMPHOCYTE
            ( I ) ORGANELLE:

( i x ) FEATURE:
            ( A ) NAME/KEY: Ja 07
            ( B ) LOCATION:
            ( C ) IDENTIFICATION METHOD:
            ( D ) OTHER INFORMATION: SEQUENCE Jα60

( x i ) SEQUENCE DESCRIPTION: SEQ ID NO: 17:

```
GGA  GCC  AAT  AGT  AAG  CTG  ACA  TTT  GGA  AAA  GGA  ATA                36
Gly  Ala  Asn  Ser  Lys  Leu  Thr  Phe  Gly  Lys  Gly  Ile
1                   5                        10

ACT  CTG  AGT  GTT  AGA  CCA  GA                                          56
Thr  Leu  Ser  Val  Arg  Pro
               15
```

( 2 ) INFORMATION FOR SEQ ID NO: 18:

( i ) SEQUENCE CHARACTERISTICS:
            ( A ) LENGTH: 57
            ( B ) TYPE: NUCLEOTIDE
            ( C ) STRANDEDNESS: DOUBLE
            ( D ) TOPOLOGY: LINEAR ( i i ) MOLECULE TYPE: cDNA to mRNA ( v i ) ORIGINAL SOURCE:
            ( A ) ORGANISM: HUMAN
            ( B ) STRAIN:
            ( C ) INDIVIDUAL ISOLATE:
            ( D ) DEVELOPMENTAL STAGE:
            ( E ) HAPLOTYPE:
            ( F ) TISSUE TYPE:
            ( G ) CELL TYPE:
            ( H ) CELL LINE: HUMAN T LYMPHOCYTE
            ( I ) ORGANELLE:

( i x ) FEATURE:
            ( A ) NAME/KEY: Ja 08
            ( B ) LOCATION:
            ( C ) IDENTIFICATION METHOD:
            ( D ) OTHER INFORMATION: SEQUENCE Jα60

( x i ) SEQUENCE DESCRIPTION: SEQ ID NO: 18:

```
CT  GGT  GGC  TAC  AAT  AAG  CTG  ATT  TTT  GGA  GCA  GGG                 35
    Gly  Gly  Tyr  Asn  Lys  Leu  Ile  Phe  Gly  Ala  Gly
    1                   5                         10

ACC  AGG  CTG  GCT  GTA  CAC  CCA  T                                      57
Thr  Arg  Leu  Ala  Val  His  Pro
               15
```

( 2 ) INFORMATION FOR SEQ ID NO: 19:

( i ) SEQUENCE CHARACTERISTICS:
            ( A ) LENGTH: 50
            ( B ) TYPE: NUCLEOTIDE
            ( C ) STRANDEDNESS: DOUBLE
            ( D ) TOPOLOGY: LINEAR ( i i ) MOLECULE TYPE: cDNA to mRNA ( v i ) ORIGINAL SOURCE:
            ( A ) ORGANISM: HUMAN
            ( B ) STRAIN:
            ( C ) INDIVIDUAL ISOLATE:
            ( D ) DEVELOPMENTAL STAGE:
            ( E ) HAPLOTYPE:
            ( F ) TISSUE TYPE:
            ( G ) CELL TYPE:
            ( H ) CELL LINE: HUMAN T LYMPHOCYTE ( I ) ORGANELLE:

( i x ) FEATURE:
                    ( A ) NAME/KEY: Ja 09
                    ( B ) LOCATION:
                    ( C ) IDENTIFICATION METHOD:
                    ( D ) OTHER INFORMATION: SEQUENCE Jα60

( x i ) SEQUENCE DESCRIPTION: SEQ ID NO: 19:

```
T  GGA  AAC  AAG  CTG  GTC  TTT  GGC  GCA  GGA  ACC  ATT                    34
   Gly  Asn  Lys  Leu  Val  Phe  Gly  Ala  Gly  Thr  Ile
   1              5                        10

CTG  AGA  GTC  AAG  TCC  T                                                   50
Leu  Arg  Val  Lys  Ser
              15
```

( 2 ) INFORMATION FOR SEQ ID NO: 20:

( i ) SEQUENCE CHARACTERISTICS:
                    ( A ) LENGTH: 22
                    ( B ) TYPE: NUCLEOTIDE
                    ( C ) STRANDEDNESS: SINGLE
                    ( D ) TOPOLOGY: LINEAR ( i i ) MOLECULE TYPE: OLIGONUCLEOTIDE ( i x ) FEATURE:
                    ( A ) NAME/KEY:
                    ( B ) LOCATION:
                    ( C ) IDENTIFICATION METHOD:
                    ( D ) OTHER INFORMATION: A ( x i ) SEQUENCE DESCRIPTION: SEQ ID NO: 20:

```
GTTGCTCCAG GCCACAGCAC TG                                                     22
```

( 2 ) INFORMATION FOR SEQ ID NO: 21:

( i ) SEQUENCE CHARACTERISTICS:
                    ( A ) LENGTH: 35
                    ( B ) TYPE: NUCLEOTIDE
                    ( C ) STRANDEDNESS: SINGLE
                    ( D ) TOPOLOGY: LINEAR ( i i ) MOLECULE TYPE: OLIGONUCLEOTIDE ( i x ) FEATURE:
                    ( A ) NAME/KEY:
                    ( B ) LOCATION:
                    ( C ) IDENTIFICATION METHOD:
                    ( D ) OTHER INFORMATION: POLY C ( x i ) SEQUENCE DESCRIPTION: SEQ ID NO: 21:

```
GCATGCGCGC GGCCGCGGAG GCCCCCCCCC CCCCC                                       35
```

( 2 ) INFORMATION FOR SEQ ID NO: 22:

( i ) SEQUENCE CHARACTERISTICS:
                    ( A ) LENGTH: 26
                    ( B ) TYPE: NUCLEOTIDE
                    ( C ) STRANDEDNESS: SINGLE
                    ( D ) TOPOLOGY: LINEAR ( i i ) MOLECULE TYPE: OLIGONUCLEOTIDE ( i x ) FEATURE:
                    ( A ) NAME/KEY:
                    ( B ) LOCATION:
                    ( C ) IDENTIFICATION METHOD:
                    ( D ) OTHER INFORMATION: B ( x i ) SEQUENCE DESCRIPTION: SEQ ID NO: 22:

```
GTCCATAGAC CTCATGTCCA GCACAG                                                 26
```

( 2 ) INFORMATION FOR SEQ ID NO: 23:

( i ) SEQUENCE CHARACTERISTICS:
        ( A ) LENGTH: 24
        ( B ) TYPE: NUCLEOTIDE
        ( C ) STRANDEDNESS: SINGLE
        ( D ) TOPOLOGY: LINEAR ( i i ) MOLECULE TYPE: OLIGONUCLEOTIDE ( i x ) FEATURE:
        ( A ) NAME/KEY:
        ( B ) LOCATION:
        ( C ) IDENTIFICATION METHOD:
        ( D ) OTHER INFORMATION: C ( x i ) SEQUENCE DESCRIPTION: SEQ ID NO: 23:

ATACACATCA GAATTCTTAC TTTG        24

( 2 ) INFORMATION FOR SEQ ID NO: 24:

( i ) SEQUENCE CHARACTERISTICS:
        ( A ) LENGTH: 19
        ( B ) TYPE: NUCLEOTIDE
        ( C ) STRANDEDNESS: SINGLE
        ( D ) TOPOLOGY: LINEAR ( i i ) MOLECULE TYPE: OLIGONUCLEOTIDE ( i x ) FEATURE:
        ( A ) NAME/KEY:
        ( B ) LOCATION:
        ( C ) IDENTIFICATION METHOD:
        ( D ) OTHER INFORMATION: D ( x i ) SEQUENCE DESCRIPTION: SEQ ID NO: 24:

GTCACTGGAT TTAGAGTCT        19

( 2 ) INFORMATION FOR SEQ ID NO: 25:

( i ) SEQUENCE CHARACTERISTICS:
        ( A ) LENGTH: 24
        ( B ) TYPE: NUCLEOTIDE
        ( C ) STRANDEDNESS: SINGLE
        ( D ) TOPOLOGY: LINEAR ( i i ) MOLECULE TYPE: OLIGONUCLEOTIDE ( i x ) FEATURE:
        ( A ) NAME/KEY:
        ( B ) LOCATION:
        ( C ) IDENTIFICATION METHOD:
        ( D ) OTHER INFORMATION: TYPE V$\alpha$1, CLONE AB22,
              POSITION 235

( x i ) SEQUENCE DESCRIPTION: SEQ ID NO: 25:

GGCATTAACG GTTTTGAGGC TGGA        24

( 2 ) INFORMATION FOR SEQ ID NO: 26:

( i ) SEQUENCE CHARACTERISTICS:
        ( A ) LENGTH: 24
        ( B ) TYPE: NUCLEOTIDE
        ( C ) STRANDEDNESS: SINGLE
        ( D ) TOPOLOGY: LINEAR ( i i ) MOLECULE TYPE: OLIGONUCLEOTIDE ( i x ) FEATURE:
        ( A ) NAME/KEY:
        ( B ) LOCATION:
        ( C ) IDENTIFICATION METHOD:

( D ) OTHER INFORMATION: TYPE Vα2, CLONE IGRa09,
POSITION 93*

( x i ) SEQUENCE DESCRIPTION: SEQ ID NO: 26:

CAGTGTTCCA GAGGGAGCCA TTGC                                            24

( 2 ) INFORMATION FOR SEQ ID NO: 27:

( i ) SEQUENCE CHARACTERISTICS:
        ( A ) LENGTH: 24
        ( B ) TYPE: NUCLEOTIDE
        ( C ) STRANDEDNESS: SINGLE
        ( D ) TOPOLOGY: LINEAR ( i i ) MOLECULE TYPE: OLIGONUCLEOTIDE ( i x ) FEATURE:
        ( A ) NAME/KEY:
        ( B ) LOCATION:
        ( C ) IDENTIFICATION METHOD:
        ( D ) OTHER INFORMATION: TYPE V α3, CLONE HAP05,
POSITION 297

( x i ) SEQUENCE DESCRIPTION: SEQ ID NO: 27:

CCGGGCAGCA GACACTGCTT CTTA                                            24

( 2 ) INFORMATION FOR SEQ ID NO: 28:

( i ) SEQUENCE CHARACTERISTICS:
        ( A ) LENGTH: 24
        ( B ) TYPE: NUCLEOTIDE
        ( C ) STRANDEDNESS: SINGLE
        ( D ) TOPOLOGY: LINEAR ( i i ) MOLECULE TYPE: OLIGONUCLEOTIDE ( i x ) FEATURE:
        ( A ) NAME/KEY:
        ( B ) LOCATION:
        ( C ) IDENTIFICATION METHOD:
        ( D ) OTHER INFORMATION: TYPE V α4, CLONE HAP08,
POSITION 153

( x i ) SEQUENCE DESCRIPTION: SEQ ID NO: 28:

TTGGTATCGA CAGCTTCCCT CCCA                                            24

( 2 ) INFORMATION FOR SEQ ID NO: 29:

( i ) SEQUENCE CHARACTERISTICS:
        ( A ) LENGTH: 24
        ( B ) TYPE: NUCLEOTIDE
        ( C ) STRANDEDNESS: SINGLE
        ( D ) TOPOLOGY: LINEAR ( i i ) MOLECULE TYPE: OLIGONUCLEOTIDE ( i x ) FEATURE:
        ( A ) NAME/KEY:
        ( B ) LOCATION:
        ( C ) IDENTIFICATION METHOD:
        ( D ) OTHER INFORMATION: TYPE Vα5, CLONE IGRa10,
POSITION 113

( x i ) SEQUENCE DESCRIPTION: SEQ ID NO: 29:

CGGCCACCCT GACCTGCAAC TATA                                            24

( 2 ) INFORMATION FOR SEQ ID NO: 30:

( i ) SEQUENCE CHARACTERISTICS:
        ( A ) LENGTH: 24
        ( B ) TYPE: NUCLEOTIDE
        ( C ) STRANDEDNESS: SINGLE (D) TOPOLOGY: LINEAR (ii) MOLECULE TYPE: OLIGONUCLEOTIDE (ix) FEATURE:
  (A) NAME/KEY:
  (B) LOCATION:
  (C) IDENTIFICATION METHOD:
  (D) OTHER INFORMATION: TYPE Vα6, CLONE HAP01,
    POSITION 287

(xi) SEQUENCE DESCRIPTION: SEQ ID NO: 30:

TCCGCCAACC TTGTCATCTC CGCT    24

(2) INFORMATION FOR SEQ ID NO: 31:

(i) SEQUENCE CHARACTERISTICS:
  (A) LENGTH: 24
  (B) TYPE: NUCLEOTIDE
  (C) STRANDEDNESS: SINGLE
  (D) TOPOLOGY: LINEAR (ii) MOLECULE TYPE: OLIGONUCLEOTIDE (ix) FEATURE:
  (A) NAME/KEY:
  (B) LOCATION:
  (C) IDENTIFICATION METHOD:
  (D) OTHER INFORMATION: TYPE Vα7, CLONE IGRall,
    POSITION 159

(xi) SEQUENCE DESCRIPTION: SEQ ID NO: 31:

GCAACATGCT GGCGGAGCAC CCAC    24

(2) INFORMATION FOR SEQ ID NO: 32:

(i) SEQUENCE CHARACTERISTICS:
  (A) LENGTH: 24
  (B) TYPE: NUCLEOTIDE
  (C) STRANDEDNESS: SINGLE
  (D) TOPOLOGY: LINEAR (ii) MOLECULE TYPE: OLIGONUCLEOTIDE (ix) FEATURE:
  (A) NAME/KEY:
  (B) LOCATION:
  (C) IDENTIFICATION METHOD:
  (D) OTHER INFORMATION: TYPE Vα8, CLONE HAP41,
    POSITION 204

(xi) SEQUENCE DESCRIPTION: SEQ ID NO: 32:

CATTCGTTCA AATGTGGGCA AAAG    24

(2) INFORMATION FOR SEQ ID NO: 33:

(i) SEQUENCE CHARACTERISTICS:
  (A) LENGTH: 24
  (B) TYPE: NUCLEOTIDE
  (C) STRANDEDNESS: SINGLE
  (D) TOPOLOGY: LINEAR (ii) MOLECULE TYPE: OLIGONUCLEOTIDE (ix) FEATURE:
  (A) NAME/KEY:
  (B) LOCATION:
  (C) IDENTIFICATION METHOD:
  (D) OTHER INFORMATION: TYPE Vα9, CLONE HAVP36,
    POSITION 168

(xi) SEQUENCE DESCRIPTION: SEQ ID NO: 33:

CCAGTACTCC AGACAACGCC TGCA    24

( 2 ) INFORMATION FOR SEQ ID NO: 34:

( i ) SEQUENCE CHARACTERISTICS:
        ( A ) LENGTH: 24
        ( B ) TYPE: NUCLEOTIDE
        ( C ) STRANDEDNESS: SINGLE
        ( D ) TOPOLOGY: LINEAR ( i i ) MOLECULE TYPE: OLIGONUCLEOTIDE ( i x ) FEATURE:
        ( A ) NAME/KEY:
        ( B ) LOCATION:
        ( C ) IDENTIFICATION METHOD:
        ( D ) OTHER INFORMATION: TYPE Vα10, CLONE HAP58, POSITION 282

( x i ) SEQUENCE DESCRIPTION: SEQ ID NO: 34:

CACTGCGGCC CAGCCTGGTG ATAC         24

( 2 ) INFORMATION FOR SEQ ID NO: 35:

( i ) SEQUENCE CHARACTERISTICS:
        ( A ) LENGTH: 24
        ( B ) TYPE: NUCLEOTIDE
        ( C ) STRANDEDNESS: SINGLE
        ( D ) TOPOLOGY: LINEAR ( i i ) MOLECULE TYPE: OLIGONUCLEOTIDE ( i x ) FEATURE:
        ( A ) NAME/KEY:
        ( B ) LOCATION:
        ( C ) IDENTIFICATION METHOD:
        ( D ) OTHER INFORMATION: TYPE Vα11, CLONE AB19, POSITION 254*

( x i ) SEQUENCE DESCRIPTION: SEQ ID NO: 35:

CGCTGCTCAT CCTCCAGGTG CGGG         24

( 2 ) INFORMATION FOR SEQ ID NO: 36:

( i ) SEQUENCE CHARACTERISTICS:
        ( A ) LENGTH: 24
        ( B ) TYPE: NUCLEOTIDE
        ( C ) STRANDEDNESS: SINGLE
        ( D ) TOPOLOGY: LINEAR ( i i ) MOLECULE TYPE: OLIGONUCLEOTIDE ( i x ) FEATURE:
        ( A ) NAME/KEY:
        ( B ) LOCATION:
        ( C ) IDENTIFICATION METHOD:
        ( D ) OTHER INFORMATION: TYPE Vα12, CLONE V12MA483, POSITION 213

( x i ) SEQUENCE DESCRIPTION: SEQ ID NO: 36:

TCGTCGGAAC TCTTTTGATG AGCA         24

( 2 ) INFORMATION FOR SEQ ID NO: 37:

( i ) SEQUENCE CHARACTERISTICS:
        ( A ) LENGTH: 24
        ( B ) TYPE: NUCLEOTIDE
        ( C ) STRANDEDNESS: SINGLE
        ( D ) TOPOLOGY: LINEAR ( i i ) MOLECULE TYPE: OLIGONUCLEOTIDE ( i x ) FEATURE:
        ( A ) NAME/KEY:

( B ) LOCATION:
                ( C ) IDENTIFICATION METHOD:
                ( D ) OTHER INFORMATION: TYPE Vα13, CLONE
                        HAVT15, POSITION 152*

( x i ) SEQUENCE DESCRIPTION: SEQ ID NO: 37:

TTCATCAAAA CCCTTGGGGA CAGC                                                      24

( 2 ) INFORMATION FOR SEQ ID NO: 38:

( i ) SEQUENCE CHARACTERISTICS:
                ( A ) LENGTH: 24
                ( B ) TYPE: NUCLEOTIDE
                ( C ) STRANDEDNESS: SINGLE
                ( D ) TOPOLOGY: LINEAR ( i i ) MOLECULE TYPE: OLIGONUCLEOTIDE ( i x ) FEATURE:
                ( A ) NAME/KEY:
                ( B ) LOCATION:
                ( C ) IDENTIFICATION METHOD:
                ( D ) OTHER INFORMATION: TYPE Vα14, CLONE
                        HAVT20, POSITION 181

( x i ) SEQUENCE DESCRIPTION: SEQ ID NO: 38:

CCCAGCAGGC AGATGATTCT CGTT                                                      24

( 2 ) INFORMATION FOR SEQ ID NO: 39:

( i ) SEQUENCE CHARACTERISTICS:
                ( A ) LENGTH: 24
                ( B ) TYPE: NUCLEOTIDE
                ( C ) STRANDEDNESS: SINGLE
                ( D ) TOPOLOGY: LINEAR ( i i ) MOLECULE TYPE: OLIGONUCLEOTIDE ( i x ) FEATURE:
                ( A ) NAME/KEY:
                ( B ) LOCATION:
                ( C ) IDENTIFICATION METHOD:
                ( D ) OTHER INFORMATION: TYPE Vα15, CLONE
                        HAVT31, POSITION 278

( x i ) SEQUENCE DESCRIPTION: SEQ ID NO: 39:

TTGCAGACAC CGAGACTGGG GACT                                                      24

( 2 ) INFORMATION FOR SEQ ID NO: 40:

( i ) SEQUENCE CHARACTERISTICS:
                ( A ) LENGTH: 24
                ( B ) TYPE: NUCLEOTIDE
                ( C ) STRANDEDNESS: SINGLE
                ( D ) TOPOLOGY: LINEAR ( i i ) MOLECULE TYPE: OLIGONUCLEOTIDE ( i x ) FEATURE:
                ( A ) NAME/KEY:
                ( B ) LOCATION:
                ( C ) IDENTIFICATION METHOD:
                ( D ) OTHER INFORMATION: TYPE Vα16, CLONE
                        IGRa13, POSITION 89

( x i ) SEQUENCE DESCRIPTION: SEQ ID NO: 40:

TCAACGTTGC TGAAGGGAAT CCTC                                                      24

( 2 ) INFORMATION FOR SEQ ID NO: 41:

( i ) SEQUENCE CHARACTERISTICS:
                ( A ) LENGTH: 24

(B) TYPE: NUCLEOTIDE
(C) STRANDEDNESS: SINGLE
(D) TOPOLOGY: LINEAR (ii) MOLECULE TYPE: OLIGONUCLEOTIDE (ix) FEATURE:
(A) NAME/KEY:
(B) LOCATION:
(C) IDENTIFICATION METHOD:
(D) OTHER INFORMATION: TYPE Vα17, CLONE AB11, POSITION 204

(xi) SEQUENCE DESCRIPTION: SEQ ID NO: 41:

TGGGAAAGGC CGTGCATTAT TGAT 24

(2) INFORMATION FOR SEQ ID NO: 42:

(i) SEQUENCE CHARACTERISTICS:
(A) LENGTH: 24
(B) TYPE: NUCLEOTIDE
(C) STRANDEDNESS: SINGLE
(D) TOPOLOGY: LINEAR (ii) MOLECULE TYPE: OLIGONUCLEOTIDE (ix) FEATURE:
(A) NAME/KEY:
(B) LOCATION:
(C) IDENTIFICATION METHOD:
(D) OTHER INFORMATION: TYPE Vα18, CLONE AB21, POSITION 114

(xi) SEQUENCE DESCRIPTION: SEQ ID NO: 42:

CAGCACCAAT TTCACCTGCA GCTT 24

(2) INFORMATION FOR SEQ ID NO: 43:

(i) SEQUENCE CHARACTERISTICS:
(A) LENGTH: 24
(B) TYPE: NUCLEOTIDE
(C) STRANDEDNESS: SINGLE
(D) TOPOLOGY: LINEAR (ii) MOLECULE TYPE: OLIGONUCLEOTIDE (ix) FEATURE:
(A) NAME/KEY:
(B) LOCATION:
(C) IDENTIFICATION METHOD:
(D) OTHER INFORMATION: TYPE Vα19, CLONE AC24, POSITION 162

(xi) SEQUENCE DESCRIPTION: SEQ ID NO: 43:

ACACTGGCTG CAACAGCATC CAGG 24

(2) INFORMATION FOR SEQ ID NO: 44:

(i) SEQUENCE CHARACTERISTICS:
(A) LENGTH: 24
(B) TYPE: NUCLEOTIDE
(C) STRANDEDNESS: SINGLE
(D) TOPOLOGY: LINEAR (ii) MOLECULE TYPE: OLIGONUCLEOTIDE (ix) FEATURE:
(A) NAME/KEY:
(B) LOCATION:
(C) IDENTIFICATION METHOD:
(D) OTHER INFORMATION: TYPE Vα20, CLONE AE212, POSITION 232

(xi) SEQUENCE DESCRIPTION: SEQ ID NO: 44:

TCCCTGTTTA TCCCTGCCGA CAGA                                                                24

( 2 ) INFORMATION FOR SEQ ID NO: 45:

( i ) SEQUENCE CHARACTERISTICS:
        ( A ) LENGTH: 24
        ( B ) TYPE: NUCLEOTIDE
        ( C ) STRANDEDNESS: SINGLE
        ( D ) TOPOLOGY: LINEAR ( i i ) MOLECULE TYPE: OLIGONUCLEOTIDE ( v i ) ORIGINAL SOURCE:
        ( A ) ORGANISM: HUMAN
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE: HUMAN T LYMPHOCYTE
        ( I ) ORGANELLE:

( i x ) FEATURE:
        ( A ) NAME/KEY:
        ( B ) LOCATION:
        ( C ) IDENTIFICATION METHOD:
        ( D ) OTHER INFORMATION: TYPE Vα21, CLONE AF211,
            POSITION 92

( x i ) SEQUENCE DESCRIPTION: SEQ ID NO: 45:

AGCAAAATTC ACCATCCCTG AGCG                                                                24

( 2 ) INFORMATION FOR SEQ ID NO: 46:

( i ) SEQUENCE CHARACTERISTICS:
        ( A ) LENGTH: 24
        ( B ) TYPE: NUCLEOTIDE
        ( C ) STRANDEDNESS: SINGLE
        ( D ) TOPOLOGY: LINEAR ( i i ) MOLECULE TYPE: OLIGONUCLEOTIDE ( i x ) FEATURE:
        ( A ) NAME/KEY:
        ( B ) LOCATION:
        ( C ) IDENTIFICATION METHOD:
        ( D ) OTHER INFORMATION: TYPE Vα22, CLONE
            IGRa12, POSITION 197

( x i ) SEQUENCE DESCRIPTION: SEQ ID NO: 46:

CCTGAAAGCC ACGAAGGCTG ATGA                                                                24

( 2 ) INFORMATION FOR SEQ ID NO: 47:

( i ) SEQUENCE CHARACTERISTICS:
        ( A ) LENGTH: 24
        ( B ) TYPE: NUCLEOTIDE
        ( C ) STRANDEDNESS: SINGLE
        ( D ) TOPOLOGY: LINEAR ( i i ) MOLECULE TYPE: OLIGONUCLEOTIDE ( i x ) FEATURE:
        ( A ) NAME/KEY:
        ( B ) LOCATION:
        ( C ) IDENTIFICATION METHOD:
        ( D ) OTHER INFORMATION: TYPE Vαw23, CLONE
            IGRa01, POSITION 246

( x i ) SEQUENCE DESCRIPTION: SEQ ID NO: 47:

TGCCTCGCTG GATAAATCAT CAGG                                                                24

( 2 ) INFORMATION FOR SEQ ID NO: 48:

( i ) SEQUENCE CHARACTERISTICS:
        ( A ) LENGTH: 24
        ( B ) TYPE: NUCLEOTIDE
        ( C ) STRANDEDNESS: SINGLE
        ( D ) TOPOLOGY: LINEAR ( i i ) MOLECULE TYPE: OLIGONUCLEOTIDE ( i x ) FEATURE:
        ( A ) NAME/KEY:
        ( B ) LOCATION:
        ( C ) IDENTIFICATION METHOD:
        ( D ) OTHER INFORMATION: TYPE Vαw24, CLONE
            IGRa02, POSITION 259

( x i ) SEQUENCE DESCRIPTION: SEQ ID NO: 48:

CTGGATGCAG ACACAAAGCA GAGC     24

( 2 ) INFORMATION FOR SEQ ID NO: 49:

( i ) SEQUENCE CHARACTERISTICS:
        ( A ) LENGTH: 24
        ( B ) TYPE: NUCLEOTIDE
        ( C ) STRANDEDNESS: SINGLE
        ( D ) TOPOLOGY: LINEAR ( i i ) MOLECULE TYPE: OLIGONUCLEOTIDE ( i x ) FEATURE:
        ( A ) NAME/KEY:
        ( B ) LOCATION:
        ( C ) IDENTIFICATION METHOD:
        ( D ) OTHER INFORMATION: TYPE Vαw25, CLONE
            IGRa03, POSITION 148

( x i ) SEQUENCE DESCRIPTION: SEQ ID NO: 49:

TGGCTACGGT ACAAGCCGGA CCCT     24

( 2 ) INFORMATION FOR SEQ ID NO: 50:

( i ) SEQUENCE CHARACTERISTICS:
        ( A ) LENGTH: 24
        ( B ) TYPE: NUCLEOTIDE
        ( C ) STRANDEDNESS: SINGLE
        ( D ) TOPOLOGY: LINEAR ( i i ) MOLECULE TYPE: OLIGONUCLEOTIDE ( i x ) FEATURE:
        ( A ) NAME/KEY:
        ( B ) LOCATION:
        ( C ) IDENTIFICATION METHOD:
        ( D ) OTHER INFORMATION: TYPE Vαw26, CLONE
            IGRa04, POSITION 299

( x i ) SEQUENCE DESCRIPTION: SEQ ID NO: 50:

AGCGCAGCCA TGCAGGCATG TACC     24

( 2 ) INFORMATION FOR SEQ ID NO: 51:

( i ) SEQUENCE CHARACTERISTICS:
        ( A ) LENGTH: 24
        ( B ) TYPE: NUCLEOTIDE
        ( C ) STRANDEDNESS: SINGLE
        ( D ) TOPOLOGY: LINEAR ( i i ) MOLECULE TYPE: OLIGONUCLEOTIDE ( i x ) FEATURE:
        ( A ) NAME/KEY:
        ( B ) LOCATION:

( C ) IDENTIFICATION METHOD:
            ( D ) OTHER INFORMATION: TYPE Vαw27, CLONE
                IGRa05, POSITION 268*

( x i ) SEQUENCE DESCRIPTION: SEQ ID NO: 51:

AAGCCCGTCT CAGCACCCTC CACA                                                              24

( 2 ) INFORMATION FOR SEQ ID NO: 52:

( i ) SEQUENCE CHARACTERISTICS:
            ( A ) LENGTH: 24
            ( B ) TYPE: NUCLEOTIDE
            ( C ) STRANDEDNESS: SINGLE
            ( D ) TOPOLOGY: LINEAR ( i i ) MOLECULE TYPE: OLIGONUCLEOTIDE ( i x ) FEATURE:
            ( A ) NAME/KEY:
            ( B ) LOCATION:
            ( C ) IDENTIFICATION METHOD:
            ( D ) OTHER INFORMATION: TYPE Vαw28, CLONE
                IGRa06, POSITION 95

( x i ) SEQUENCE DESCRIPTION: SEQ ID NO: 52:

TGGTTGTGCA CGAGCGAGAC ACTG                                                              24

( 2 ) INFORMATION FOR SEQ ID NO: 53:

( i ) SEQUENCE CHARACTERISTICS:
            ( A ) LENGTH: 24
            ( B ) TYPE: NUCLEOTIDE
            ( C ) STRANDEDNESS: SINGLE
            ( D ) TOPOLOGY: LINEAR ( i i ) MOLECULE TYPE: OLIGONUCLEOTIDE ( v i ) ORIGINAL SOURCE:
            ( A ) ORGANISM: HUMAN
            ( B ) STRAIN:
            ( C ) INDIVIDUAL ISOLATE:
            ( D ) DEVELOPMENTAL STAGE:
            ( E ) HAPLOTYPE:
            ( F ) TISSUE TYPE:
            ( G ) CELL TYPE:
            ( H ) CELL LINE: HUMAN T LYMPHOCYTE
            ( I ) ORGANELLE:

( i x ) FEATURE:
            ( A ) NAME/KEY:
            ( B ) LOCATION:
            ( C ) IDENTIFICATION METHOD:
            ( D ) OTHER INFORMATION: TYPE Vαw29, CLONE
                IGRa07, POSITION 210

( x i ) SEQUENCE DESCRIPTION: SEQ ID NO: 53:

GAAGGGTGGA GAACAGATGC GTCG                                                              24

( 2 ) INFORMATION FOR SEQ ID NO: 54:

( i ) SEQUENCE CHARACTERISTICS:
            ( A ) LENGTH: 24
            ( B ) TYPE: NUCLEOTIDE
            ( C ) STRANDEDNESS: SINGLE
            ( D ) TOPOLOGY: LINEAR ( i i ) MOLECULE TYPE: OLIGONUCLEOTIDE ( i x ) FEATURE:
            ( A ) NAME/KEY:
            ( B ) LOCATION:
            ( C ) IDENTIFICATION METHOD:
            ( D ) OTHER INFORMATION: TYPE C±A, POSITION 129

-continued (xi) SEQUENCE DESCRIPTION: SEQ ID NO: 54:

ATACACATCA GAATTCTTAC TTTG     24

(2) INFORMATION FOR SEQ ID NO: 55:

(i) SEQUENCE CHARACTERISTICS:
        (A) LENGTH: 24
        (B) TYPE: NUCLEOTIDE
        (C) STRANDEDNESS: SINGLE
        (D) TOPOLOGY: LINEAR (ii) MOLECULE TYPE: OLIGONUCLEOTIDE (ix) FEATURE:
        (A) NAME/KEY:
        (B) LOCATION:
        (C) IDENTIFICATION METHOD:
        (D) OTHER INFORMATION: TYPE C±B, POSITION 201

(xi) SEQUENCE DESCRIPTION: SEQ ID NO: 55:

GTTGCTCCAG GCCGCGGCAC TGTT     24

(2) INFORMATION FOR SEQ ID NO: 56:

(i) SEQUENCE CHARACTERISTICS:
        (A) LENGTH: 19
        (B) TYPE: NUCLEOTIDE
        (C) STRANDEDNESS: SINGLE
        (D) TOPOLOGY: LINEAR (ii) MOLECULE TYPE: OLIGONUCLEOTIDE (ix) FEATURE:
        (A) NAME/KEY:
        (B) LOCATION:
        (C) IDENTIFICATION METHOD:
        (D) OTHER INFORMATION: TYPE C±C, POSITION 57

(xi) SEQUENCE DESCRIPTION: SEQ ID NO: 56:

GTCACTGGAT TTAGAGTCT     19

(2) INFORMATION FOR SEQ ID NO: 57:

(i) SEQUENCE CHARACTERISTICS:
        (A) LENGTH: 24
        (B) TYPE: NUCLEOTIDE
        (C) STRANDEDNESS: SINGLE
        (D) TOPOLOGY: LINEAR (ii) MOLECULE TYPE: OLIGONUCLEOTIDE (ix) FEATURE:
        (A) NAME/KEY:
        (B) LOCATION:
        (C) IDENTIFICATION METHOD:
        (D) OTHER INFORMATION: TYPE Act 1, CLONE Ã-actin, POSITION 1161

(xi) SEQUENCE DESCRIPTION: SEQ ID NO: 57:

ATTTGCGGTG GACGATGGAG GGGC     24

(2) INFORMATION FOR SEQ ID NO: 58:

(i) SEQUENCE CHARACTERISTICS:
        (A) LENGTH: 24
        (B) TYPE: NUCLEOTIDE
        (C) STRANDEDNESS: SINGLE
        (D) TOPOLOGY: LINEAR (ii) MOLECULE TYPE: OLIGONUCLEOTIDE (ix) FEATURE:

(A) NAME/KEY:
        (B) LOCATION:
        (C) IDENTIFICATION METHOD:
        (D) OTHER INFORMATION: TYPE Act 2, CLONE Ã-
            ACTIN, POSITION 261

(xi) SEQUENCE DESCRIPTION: SEQ ID NO: 58:

GGCATCGTCA CCAACTGGGA CGAC  24

(2) INFORMATION FOR SEQ ID NO: 59:

(i) SEQUENCE CHARACTERISTICS:
        (A) LENGTH: 19
        (B) TYPE: NUCLEOTIDE
        (C) STRANDEDNESS: SINGLE
        (D) TOPOLOGY: LINEAR (ii) MOLECULE TYPE: OLIGONUCLEOTIDE (ix) FEATURE:
        (A) NAME/KEY:
        (B) LOCATION:
        (C) IDENTIFICATION METHOD:
        (D) OTHER INFORMATION: TYPE Act 3, CLONE Ã-
            ACTIN, POSITION 642

(xi) SEQUENCE DESCRIPTION: SEQ ID NO: 59:

ACCACCACGG CGGAGCGGG  19

(2) INFORMATION FOR SEQ ID NO: 60:

(i) SEQUENCE CHARACTERISTICS:
        (A) LENGTH: 24
        (B) TYPE: NUCLEOTIDE
        (C) STRANDEDNESS: SINGLE
        (D) TOPOLOGY: LINEAR (ii) MOLECULE TYPE: OLIGONUCLEOTIDE (ix) FEATURE:
        (A) NAME/KEY:
        (B) LOCATION:
        (C) IDENTIFICATION METHOD:
        (D) OTHER INFORMATION: TYPE CÃF, POSITION 135

(xi) SEQUENCE DESCRIPTION: SEQ ID NO: 60:

CGGGCTGCTC CTTGAGGGGC TGCG  24

(2) INFORMATION FOR SEQ ID NO: 61:

(i) SEQUENCE CHARACTERISTICS:
        (A) LENGTH: 19
        (B) TYPE: NUCLEOTIDE
        (C) STRANDEDNESS: SINGLE
        (D) TOPOLOGY: LINEAR (ii) MOLECULE TYPE: OLIGONUCLEOTIDE (ix) FEATURE:
        (A) NAME/KEY:
        (B) LOCATION:
        (C) IDENTIFICATION METHOD:
        (D) OTHER INFORMATION: TYPE CÃK, POSITION 20

(xi) SEQUENCE DESCRIPTION: SEQ ID NO: 61:

CCCACCCGAG GTCGCTGTG  19

(2) INFORMATION FOR SEQ ID NO: 62:

(i) SEQUENCE CHARACTERISTICS:
        (A) LENGTH: 19
        (B) TYPE: NUCLEOTIDE

```
        ( C ) STRANDEDNESS: SINGLE
        ( D ) TOPOLOGY: LINEAR ( i i ) MOLECULE TYPE: OLIGONUCLEOTIDE ( i x ) FEATURE:
        ( A ) NAME/KEY:
        ( B ) LOCATION:
        ( C ) IDENTIFICATION METHOD:
        ( D ) OTHER INFORMATION: TYPE CÃC, POSITION 58

( x i ) SEQUENCE DESCRIPTION: SEQ ID NO: 62:

TCTGCTTCTG ATGGCTCAA                                        1 9
```

NUCLEOTIDE SEQUENCES FOR α CHAIN VARIABLE REGIONS IN HUMAN LYMPHOCYTE RECEPTORS, CORRESPONDING PEPTIDE SEGMENTS AND THE DIAGNOSTIC AND THERAPEUTIC USES

PRIOR APPLICATION

This application is a division of U.S. patent application Ser. No. 348,572 filed Apr. 19, 1995 which is a continuation of U.S. patent application Ser. No. 934,529 filed Nov. 24, 1992, now abandoned.

The present invention relates to new nucleotide sequences coding for variable regions of α chain T-cell receptors, corresponding peptided segments and the diagnostic and therapeutic uses.

It is known that the receptors recognizing antigens at the surface of mature T lymphocytes (hereafter designated T-cell receptors) possess a structure having a certain similarity with those of immunoglobulins. Therefore, they contain heterodimeric structures containing α and β glycoprotein chains or γ and δ glycoprotein chains (see Meuer et al. (1), Moingeon et al. (2), Brenner et al. (3), Bank et al. (4)).

The directory of T-cell receptors must be able to address the immense diversity of antigenic determinants. This is obtained by genetic recombination of different discontinuous segments of genes which code for the different structural regions of T-cell receptors. Thus, the genes contain V segments (variable segments), optionally D segments (diversity segments), J segments (junction segments) and C segments (constant segments). During the differentiation of T-cells, specific genes are created by recombination of V, D and J segments for the β and δ loci and V and J segments for the α and γ loci. These specific combinations as well as the pairing of two chains create the combinational diversity. This diversity is highly amplified by two supplementary mechanisms, namely the imprecise recombination of V-D-J or V-J segments and the addition of nucleotides corresponding to the N region (Davis et al. (5).

A certain number of genetic V segments are already known. These segments have been grouped into subfamilies as a function of the similarity of sequences. By definition, the segments which have more than 75% similarity in the nucleotide sequence have been considered as members of the same subfamily (Crews et al. (6)). The known Vα genetic segments have also been classified into 22 subfamilies, 14 of which have only one member (see Concannon et al. (7), Kimura et al. (8), Wilson et al. (9)).

Moreover, about 60 J genetic segments have been described (9).

Furthermore, monoclonal antibodies directed against specific segments of the variable parts of T-cell receptors, in particular the β or δ chains, were recently described in WO 90/06758. These monoclonal antibodies are useful not only as diagnostic tools but also as therapeutic tools, for example, vis-a-vis rheumatoid arthritis.

The use of synthetic peptides corresponding to the variable regions of the α or β chains in the treatment of auto-immune diseases is also described (23 and 24).

It is also known that variations exist from one individual to another in the expression of different variable segments of the T-cell receptor in man (27 and 28).

The present inventions aims to enrich the directory of genetic segments coding for the variable regions of the chains of T-cell receptors by providing on the one hand new Vα genetic segments belonging to new subfamilies or belonging to subfamilies of which at least one member is already known, and on the other hand, new Jα genetic segments.

Therefore a subject of the present invention is nucleotide sequences coding for the variable regions of α chains of human T lymphocyte receptors, corresponding to cDNA's containing nucleotide sequences chosen from any one of the following:

a—Vα segments corresponding to one of the sequences SEQ ID No. 1 to 11, and b—Jα segments corresponding to one of the sequences SEQ ID No. 12, 13 and 14 to 19, and the sequences which differ from them by one or more nucleotides.

More particularly a subject of the present invention is:

sequences coding for the variable regions of α-chains of human T lymphocyte receptors, corresponding to cDNAs containing nucleotide sequences chosen from any one of the Vα segments corresponding to one of the sequences SEQ ID No. 1 to 10 and the sequences which differ from them by one or more nucleotides, sequences coding for the variable regions of α chains of human T lymphocyte receptors, corresponding to cDNAs containing nucleotide sequences chosen from any one of the Jα segments corresponding to one of the sequences SEQ ID No. 12, 13 and 14 to 19 and the sequences which differ from them by one or more nucleotides.

The expression "and sequences which differ from them by one or more nucleotides", encompasses alleles which differ by up to 8 nucleotides, but more often differ by 1 or 2 nucleotides or which can differ by the deletion or addition of one or two codons.

Also a more particular subject of the invention is:

nucleotide sequences coding for the variable regions of α chains of human T lymphocyte receptors, corresponding to cDNAs corresponding to all or part of the nucleotide sequences chosen from any one of the Vα segments corresponding to one of the sequences SEQ ID No. 2 to 5, and the sequences which differ from them by one or two nucleotides, nucleotide sequences coding for the variable regions of the α chains of human T lymphocyte receptors, corresponding to cDNAs corresponding to all or part of the nucleotide sequences chosen from any one of the Vα segments corresponding to one of the sequences 1 to 200 of SEQ ID No. 1
1 to 467 of SEQ ID No. 6
1 to 77 of SEQ ID No. 7
1 to 151 of SEQ ID No. 8
291 to 386 of SEQ ID No. 9
1 to 260 of SEQ ID No. 10 and the sequences which differ from them by one or two nucleotides, nucleotide sequences coding for the variable regions of the δ chains of human T lymphocyte receptors, corresponding to cDNAs corresponding to all or part of the nucleotide sequence corresponding to SEQ ID No. 11 and which contain the 108 nucleotide, nucleotide sequences coding for the variable regions of the α chains of human T lymphocyte receptors, corresponding to cDNAs corresponding to all or part of the nucleotide sequences chosen from any one of the Jα segments corresponding to one of the sequences SEQ ID No. 12, 13 and 14 to 19 and the sequences which differ from them by one or two nucleotides.

By the expression "nucleotide sequences corresponding to cDNAs corresponding to all or part of the nucleotide sequences" is also designated the complete sequences as well as fragments of these sequences including short fragments (oligonucleotides) which can be used as probes (generally containing at least 10 nucleotides) or as primers (generally containing at least 15 nucleotides). In a general fashion, the invention encompasses the group of new oligonucleotides which are fragments of Vα and Jα sequences according to the invention.

As to the sequences which differ by one or two nucleotides, they correspond to variations which are observed experimentally at the time of determination of the nucleotide sequence of several cDNAs.

Also a subject of the present invention is the peptides coded by the nucleotide sequences according to the invention as well as the alleles and the derivatives of the latter which have the same function.

Also a subject of the present invention is the peptides constituted by or composed of a peptide sequence coded by all or part of the sequence 108 to 364 of SEQ ID No. 11.

In a general fashion, the present invention encompasses the peptides constituted by or composed of a peptide sequence coded by the nucleotide sequences according to the invention as well as fragments of these peptides. It also encompasses the peptides which differ from the latter by one or more amino acids and which have the same function. These peptides can correspond to modifications such as those known with muteins or to allelic variations. In fact it has been shown in particular that certain genetic segments coding for the variable regions of chains of T receptors in man were subjected to a phenomenon of genetic polymorphism called allelic variation (25). The present invention encompasses the peptides resulting from this phenomenon.

The nucleotide sequences according to the invention have been obtained according to the following stages:

- isolation of the RNA's of peripheral lymphocytes of an individual;
- obtaining the complementary DNA using reverse transcriptase and a primer A which is specific to the Cα region (SEQ ID No. 20);
- genetic amplification (by Anchored Polymerase Chain Reaction or A-PCR) using a DNA polymerase, a poly C primer (SEQ ID No. 21) and a primer B which is specific to the Cα region (SEQ ID No. 22);
- a new amplification by A-PCR using DNA polymerase and a primer C which is specific to the Cα region (SEQ ID No. 23);
- insertion in a plasmid vector;
- transformation of a bacterial host with the recombinant vector;
- screening of recombinant bacterial colonies with a labelled oligonucleotide D which is specific to Cα (SEQ ID No. 24);
- extraction of plasmids from positive colonies;
- and sequencing of DNA fragments containing the Cα region.

The present invention can be reproduced, in particular, by bispecific genetic amplification (polymerase chain reaction or PCR) by starting with the peripheral lymphocytes which express the mRNA including the variable or junctional segments corresponding to sequences ID No. 1 to 13 and 14 to 19 of the invention or alternatively by applying this PCR technique to genomic DNA of any somatic cell of an individual taken at random. The invention can also be reproduced by preparing the above genetic sequences by the chemical synthesis of oligonucleotides.

The peptides according to the invention can be obtained by standard peptide synthesis. They can also be obtained by the application of known genetic engineering techniques including the insertion of a DNA sequence coding for a peptide according to the invention into an expression vector such as a plasmid and the transformation of cells with this expression vector.

Therefore a subject of the present invention is also plasmids and expression vectors containing a DNA sequence coding for a peptide according to the invention as well as the hosts transformed with this vector.

Also a subject of the present invention is antibodies, and, in particular, monoclonal antibodies directed, against an antigenic determinant belonging to or composed of a peptide according to the invention.

The monoclonal antibodies may be obtained by any of the techniques which allow the production of antibody molecules from cell line culture. These techniques include different techniques using hybridomas.

The antibody production may be obtained in animals by the immunization of the animals by injection with the peptides or fragments according to the invention, whether they be natural, recombinant or synthetic, optionally after coupling to an immunogen such as tetanic anatoxin, or also by injection of human T lymphocytes expressing the corresponding sequences at their surface, including recombinant cells transfected with the corresponding coding sequences.

Also a subject of the present invention is hybridomas producing monoclonal antibodies directed against the polypeptides according to the invention.

The present invention also encompasses the fragments and the derivatives of monoclonal antibodies according to the invention which are reactive with defined variable regions of T-cell receptors. These fragments are, in particular, the F(ab')$_2$ fragments which can be obtained by the enzymatic cleavage of antibody molecules with pepsin, the Fab' fragments which can be obtained by reduction of the disulphide bridges of F(ab')$_2$ fragments and the Fab fragments which can be obtained by the enzymatic cleavage of antibody molecules with papain in the presence of a reducing agent. These fragments can also be obtained by genetic engineering.

The monoclonal antibody derivatives are for example antibodies or fragments of these antibodies to which labellers such as a radio-isotope are attached. The monoclonal antibody derivatives are also antibodies or fragments of these antibodies to which therapeutically active molecules are attached, in particular, cytotoxic compounds.

The products of the invention have several uses in the field of diagnostics and in the field of therapeutics.

1—Uses in the field of diagnostics

The oligonucleotides contained in the nucleotide sequences according to the invention can be used to constitute detection probes (generally at least 10 nucleotides) which are capable of hybridizing with a variable region of the α-chain or primers for the amplification of DNA (generally containing at least 15 nucleotides and preferably at least 17 nucleotides) which are capable of being linked to a sequence to be amplified.

Thus the oligonucleotides are used in the diagnosis of immune disorders by detecting the presence of nucleic acid sequences which are homologues of a gene coding for the variable regions of α-chains of T-cell receptors in the mRNA of a sample from a patient. Different methods can be used to establish a connection between the expression of T-cell genes and an illness. These methods include:

a—the production and analysis of cDNA expression libraries obtained from T-cells connected with the illness to determine the frequency of dominant genes;

b—Southern blot analysis of samples of genomic DNA to determine whether genetic polymorphisms or rearrangements of the genes coding for the T-cell receptors exist;

c—the analysis of samples by obtaining cDNA, amplification by PCR and hybridization with labelled probes;

d—the hybridization in situ of T-cells without culture of T-cells beforehand.

The primers are used in PCR reactions in a method such as that defined in c above.

The monoclonal antibodies, the fragments or the derivatives of these antibodies according to the invention, in particular the anti Vα antibodies, can be used to study T-type immune responses, for example in the field of the auto-immune diseases of oncology, of allergies, of transplants and of infectious diseases. In particular, the directory of different variable α segments of the T receptor can be studied, whether it be blood or tissue T-cells. In a general fashion the techniques used can be in vitro or in vivo methods.

With in vitro methods, the samples used can be samples of body fluids or tissue samples. The techniques used can include in particular flow cytofluorimetry to analyse blood T lymphocytes or labelling with immunoperoxidase on an anatomopathological section to study the lymphocytes infiltrating the tissues.

With in vivo methods, the antibodies, their fragments or their derivatives are administered by the usual routes, for example by intravenous route, and the immunospecific linkages are detected. This can be obtained for example in the case where an antibody is used which is labelled with a radio-isotope.

2—Uses in the therapeutic field

The oligonucleotides contained in the nucleotide sequences according to the invention can be used in therapeutics as anti sense oligonucleotides. In fact it is known that it is possible in vitro to inhibit the expression of a transcript gene in human lymphocytes by incubating these lymphocytes with an anti sense oligonucleotide specific to the gene in question (26). These anti sense oligonucleotides generally contain at least 10 and, preferably, at least 16 nucleotides. These anti sense oligonucleotides can be in particular the inverted and complemented sequences corresponding to 20 nucleotides upstream from the initiation site of the translation (ATG). The significance of the use in vitro of anti sense oligonucleotides specific to a Vα or Jα genetic segment is to abolish (or strongly diminish) the expression of a T receptor containing this Vα or Jα segment and thus to obtain a phenomenon of clonal deletion at the level of the specific reactivity of T lymphocytes. The anti sense oligonucleotides can not only be used in vitro on human T lymphocytes which are then reinjected, but also in vivo by local or systemic injection preferably after modification to increase the stability in vivo and the penetration into the T lymphocytes of these oligonucleotides.

The monoclonal antibodies according to the invention, in particular the anti Vα antibodies can be used to modulate the immune system. It is in this way that the antibodies can be administered to block the interaction of the effector T-cells with their specific antigen. Anti T receptor antibodies linked for example to a cytotoxic molecule or a radio-isotope can also be administered in a way so as to obtain a clonal deletion, thanks to the specific fixation on an α chain of a T-cell receptor. The monoclonal antibodies according to the invention can be used in therapeutics at low mitogenic concentrations so as to activate, in a specific fashion, certain sub-assemblies of T-cells or can be used at much higher concentrations to fix them to the receptors concerned and thus label these sub-assemblies with a view to their elimination by the reticuloendothelial system. An important criterion in the treatment of an illness is the ability to modulate the sub-assemblies of T-cells linked with an illness. The exact nature of this therapeutic modulation, namely blocking or suppressing a particular sub-assembly of T-cells or on the contrary stimulating and activating a particular sub-assembly, will depend on the illness in question and the specific sub-assembly of T-cells concerned.

This type of treatment has an advantage over current treatments using antibodies such as the treatment with anti CD3 antibodies in patients having had a kidney transplant and having a rejection problem, given that thanks to the invention there will be no modulation of the totality of the T-cell population but only of the sub-assembly of T-cells expressing the α sub-family specific to the T-cell receptors.

Moreover, as the response of T-cells is often oligoclonal, it is generally convenient to use "cocktails" of several antibodies in therapeutics.

In addition anti Vα antibodies can be used to select T lymphocytes in vitro, for example by passing through a column containing spheres carrying the antibody. This separation of certain T lymphocytes can be used with a view to culturing these lymphocytes before reinjection into the patient.

Moreover, all or part of the peptide sequences according to the invention can be used in therapeutics, that is to say the peptide sequences coded by the nucleotide sequences according to the invention or fragments of these sequences (generally containing at least 8 to 10 amino acids). These sequences or these fragments, administered to humans or animals, can act as a decoy, that is to say they fix themselves on the epitope carried by the harmful antigen and stop the reaction of normal T-cells with the antigen, preventing in this way the development of an illness which is aggressive towards the self determinants. They can also be used as immunogens in the manufacture of vaccines (optionally after conjugation with protein carriers).

The present invention will be described in greater detail hereafter by referring to the annexed figures in which:

BRIEF DESCRIPTION OF THE DRAWINGS

FIGS. 1A to E show in a line both a known V sequence and a partial sequence of an extension according to the invention for the respective sequences SEQ ID No. 6 to 10, marked IGRa 08 to IGRa 12. In these figures, the numbering of nucleotides starts at the ATG initiation codon (which is underlined). The dots indicate identical nucleotides. The sequences which are assumed to be the leader sequences have a line over them.

FIG. 2 shows in a line the new Jα sequences (SEQ ID No. 12, 13 and 14 to 19) marked IGRJa 01, 02 and 04 to 09. In these sequences the recombination signals of the germinal line are underlined. The amino acids corresponding to highly preserved codons are marked above the sequences. The codons corresponding to a substitution in one position of a preserved amino acid are underlined twice.

Figure 3:
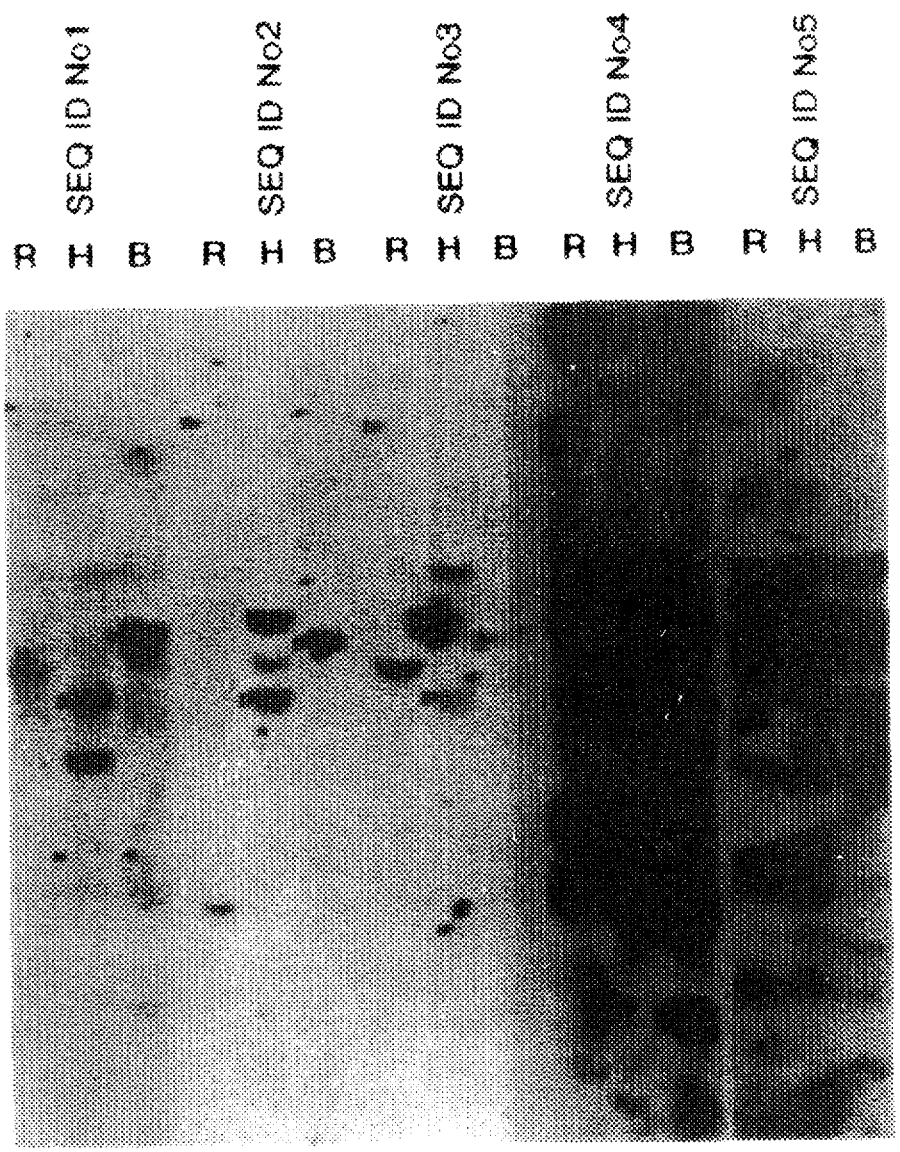
FIG. 3 shows the Southern blot analyses of the genomic DNA treated with a restriction enzyme using probes specific to sequences SEQ ID No. 1 to 5. The restriction enzymes used are EcoRI (column R), Hind III (column H) and Bam III (column B). On this figure the triangles mark the position of DNA fragments hybridizing in a specific fashion with Cα.

I—Obtaining the cDNA and Amplification by PCR

The peripheral lymphocytes of an individual are used as the DNA source. The total RNA was prepared according to the method using guanidinium isothiocyanate and caesium chloride (Chirgwin (10)) or according to a one-stage method by extraction with guanidinium isothiocyanate, phenol and chloroform (Chomcyznski (11)).

The first cDNA strand was synthesized in a final volume of 50 microliters at a temperature of 42° C. for 1 hour using 5 micrograms of total RNA, reverse transcriptase and a primer A which is specific to the Cα region constituted by the sequence 5'-GTTGCTCCAGGCCACAGCACTG (SEQ ID No. 20). This material was then purified by extraction with phenol/chloroform and precipitation with ammonium acetate. After selecting a 0.4%1 kb fraction on agarose gel, the addition of a dG end is carried out on the RNA/cDNA hetero complex in a $CoCl_2$ addition buffer with 14 units of terminal deoxynucleotidyl transferase (TdT) for 30 minutes at 37° C. The reaction was stopped by maintenance at 70° C. for 10 minutes. 1N NaOH (⅓ volume) was added and the sample was incubated at 50° C. for 1 hour to hydrolyze the RNA, then neutralized with Tris HCl 2M pH 8 and 1N HCl. After extraction with a phenol/chloroform mixture the first cDNA strand at end G was precipitated with ethanol and subjected to an amplification using the PCR technique (Polymerase Chain Reaction described by Saiki et al. (12)) in a final volume of 100 microliters containing 50 mM of KCl, 10 mM of Tris-Cl pH 8.3, 1.5 mM of $MgCl_2$, 0.1% (weight/volume) of gelatine, 200 micromoles of dNTP, 2.5 units of Taq polymerase and 100 picomoles of two primers. The two primers used are, on the one hand a poly-C primer (5'-GCATGCGCGCGGCCGCGGAGG-14C) (SEQ ID No.21) described by Loh et al. (13) as well as a primer B specific to the Cα region (5'-GTCCATAGACCTCATGTCCAGCACAG) (SEQ ID No. 22).

25 amplification cycles are carried out followed by a final 15 minute elongation period at 72° C. Each cycle includes a denaturation stage at 92° C. for 1 minute, a hybridization stage at 55° C. for 2 minutes and an elongation period at 72° C. for 4 minutes. The amplified products are then precipitated with ethanol, resuspended in 30 mM of sodium acetate pH 5, 50 mM NaCl, 1 mM $ZnCl_2$, glycerol 5% by volume and ⅒ of this material is purified as a function of size on a 1% low melting point agarose gel.

A second amplification phase is then carried out directly on approximately 10% of the band containing the agarose following the same conditions as previously, except that the primer 5'-ATACACATCAGAATTCTTACTTTG (SEQ ID No. 23) is used as primer C which is specific to the Cα region. The reaction mixture is then precipitated with ethanol and resuspended in 60 μl of $H_2O$.

II—Cloning and Sequencing of cDNA's

⅓ of the product of the second amplification is digested with Sac II, separated on 1% agarose gel and purified by absorption on glass beads. The material is inserted in the Bluescript SK⁺ vector (Stratagene, La Jolla, U.S.A.) and the recombinants obtained are used to transform the XL1-blue strains of E. Coli (Stratagene). After sedimentation in the presence of X-gal and IPTG, a test is carried out on the white colonies using a "dot blot" technique and a third oligonucleotide specific to the Cα region (5'-GTCACTGGATTTAGAGTCT) (SEQ ID No. 24) labelled with $^{32}P$ is used as a probe. The plasmid DNA of positive colonies is extracted and sequencing takes place under the two strands by the process of termination of the dideoxy chain (Sanger et al. (14)) with Sequenase 2.0 (United States Biochemicals, Cleveland, U.S.A.) following the supplier's recommendations. With the exception of the Sequence SEQ ID No. 5, all the nucleotide sequences were determined on the two strands using at least two distinct clones of cDNA.

The sequences obtained were compared with published Vα and Jα sequences using the method developed by Lipman and Pearson (15). The presumed start codons were identified by searching for the presence of the Kozak consensus sequence for the initiation sites of translations in the eukaryotic cells (Kozak (16)). The presence of hydrophobic leader sequences of the N-terminal side was detected by analysis of the hydrophobicity according to the method described by Kyte (17).

III—Southern Blot Analysis

The DNA was extracted from the human erythroleucemic cell line K562 and digested with one of the following restriction enzymes: EcoR I, BamH I or Hind III. The DNA (15 micrograms) was subjected to electrophoresis on 0.7% agarose and transferred onto Nylon membranes as described by Triebel et al. (18). The hybridizations were carried out at 65° C. with 6×SSC, 0.5% of SDS, 5×Denhardt's and 100 micrograms of denatured salmon sperm DNA for 16 hours. The membranes were washed at 65° C. with 2×SSC, 0.2% of SDS.

As Vα specific probes, are used the probes obtained by amplification of V-J-C cDNA (>500 bp) containing Vα fragments corresponding to sequences SEQ ID No. 1 to 5 using as a primer the poly-C primer and the C primer. The probes were purified on 1% agarose gel. DNA probes labelled with $^{32}P$ were prepared from fragments purified on agarose by the Feinberg method (19).

IV—Results

By using the A-PCR method, 308 cDNA which hybridize with the Cα clone were cloned, then sequenced. Among these, 172 cDNA correspond to the V-J-Cα variable regions only.

The Vα and Jα sequences of the invention are shown in the list of sequences under SEQ ID No. 1 to 11 and SEQ ID No. 12, 13 and 14 to 19 respectively. The sequences SEQ ID No. 2 to 5 correspond to the new sub-families (designated Vα25, Vα26, Vα27 and Vα29 respectively) while the sequences SEQ ID No. 1 and 6 to 11 correspond to extensions of known V segments.

1. Vα sequences corresponding to new sub-families

The Southern blot analyses of germinal line DNA subjected to digestion by endonucleases, using V-J-Cα probes containing Vα fragments corresponding to sequences SEQ ID No. 2 to 5 were carried out in "low stringency" hybridization conditions to identify the number of Vα genetic segments belonging to each family and to characterize the DNA restriction fragments carrying these Vα genetic segments. The representative results are shown in FIG. 3.

These analyses show that the sub-family corresponding to the sequence SEQ ID No. 3 includes at least two genetic segments while the other sequences (SEQ ID No. 2, No. 4 and No. 5) probably correspond to unique members.

The sizes of the germinal DNA restriction fragments are as follows:

SEQ ID No. 2: EcoR I 2.2 kb, Hind III 4.8 and 5.7 kb, BamH I 25 kb

SEQ ID No. 3: EcoR I 4.6 and 7.5 kb, Hind III 4.2 and 6.4 kb, BamH I 23 and 4.5 kb SEQ ID No. 4: EcoR I 7.6 kb, Hind III 18 kb, BamH I 9 and 0.9 kb SEQ ID No. 5: EcoR I 5.9 and 4.8 kb, Hind III 6.6 kb, BamH I 6.5 kb.

2. Sequences corresponding to extensions of known V sequences

SEQ ID No. 1 (IGR a 02) corresponds to an extension of the 5' side of the LINV sequence (171 bp) (mengle-Gaw (20)): This sequence defines the sub-family provisionaly designated Vαw24.

SEQ ID No. 6 (IGR a 08): this sequence corresponds to an extension of the 5' side of the Vα1 AE11 clone sequence (Klein et al. (21)). The two straight line sequences are represented in FIG. 1A.

SEQ ID No. 7 (IGR a 09): This sequence corresponds to an extension coding for the NH2 terminal end of the Vα2 AF110 sequence (Klein already quoted). The two straight line sequences are represented in FIG. 1B. The sequence ID No. 7 corresponds to a consensus sequence. The existence of a T instead of a C is observed in position 206.

SEQ ID No. 8 (IGR a 010): This sequence corresponds to an extension of the 5' region of the Vα HAP35 clone (Yoshikai (22)). The two straight line sequences are represented in FIG. 1C. The sequence ID No. 8 corresponds to a consensus sequence. The existence of a G instead of an A in position 307 and the existence of a T instead of a C in position 360 have been observed.

SEQ ID No. 9 (IGR a 11): This sequence corresponds to an extension of the 3' side of the Vα7 HAP12 sequence (Yoshikai already quoted). The straight line of the sequences is represented in FIG. 1D. The sequence ID No. 9 corresponds to a consensus sequence. The existence of a C instead of a T in position 86 has been observed.

SEQ ID No. 10 (IGR a 12): This sequence includes the complete coding region of a gene of the Vα22 sub-family which had been previously identified by the partial sequence (113 bp) AC9 (Klein already quoted). The two straight line sequences are represented in FIG. 1E.

SEQ ID No. 11 (IGR a 13): This sequence corresponds in part to the HAVT 32 and HAVT 35 clones (belonging to the Vα16 (8) sub-family and which have been described as pseudogenes. In fact, following the addition of a nucleotide in position 108, the SEQ ID No. 11 codes for an original variable region of a T lymphocyte receptor. Moreover, this sequence is equivalent to a sequence HSTCAYM (Klein et al. (21)) for the coding part. However, the sequence SEQ No. 11 is the only one which is complete and coding.

3. Jα sequences

The set of new Jα sequences are represented in FIG. 2. Among the 8 Jα segments, the majority of them have a highly preserved amino acid sequence FGXGT of Jα segments as described by Yoshikai already quoted. However, for the IGRJa 07 segment the threonine residue is replaced by an isoleucine residue.

In addition, instead of a phenylalanine residue a cysteine residue is found in IGRJa 02G.

The present invention also aims at providing specific oligonucleotides of different Vα sub-families, which can be used as primers for the amplification of DNA corresponding to these different Vα sub-families, with a view, for example, of a study of the expression of certain Vα sub-families in a patient and finally of a diagnosis of immune disorders, as indicated above.

The predominant expression of certain Vα sub-families has already been studied using an incomplete range of oligonucleotides. In this way Nitta et al. (29) have described the predominant expression of Vα7 genes in the lymphocytes infiltrating the tumours. Moreover, Sottini et al. (30) have described the study of the directory of Vα's, in patients suffering from rheumatoid arthritis.

The present invention aims to provide a complete range of oligonucleotides allowing the study, of both known Vα sub-families and new Vα sub-families of the invention and which are completely specific to each sub-family. Thus the oligonucleotides have been chosen and synthesized to this end and to the requirements of modifications of one or two nucleotides which have been introduced relative to the natural sequences to reduce the cross-reactions between sub-families.

Thus a subject of the present invention is also oligonucleotides which can be used as primers for the amplification of DNA corresponding to the variable regions of α chains of T-cell receptors, chosen from the sequences SEQ ID No. 25 to 53.

Also a subject of the present invention is the use, as primers for the amplification of DNA corresponding to the variable regions of α chains of T-cell receptors, of oligonucleotides chosen from the sequences SEQ ID No. 25 to 53.

Also a subject of the present invention is a detection process of nucleotide sequences coding for the Vα segments of T receptors or of cDNA corresponding to transcription products of the latter, in a biological sample, characterized in that it includes:

a) the amplification of DNA with at least one pair of primers formed by one of the oligonucleotides chosen from the sequences SEQ ID No. 25 to 53 and one oligonucleotide belonging to segment Cα, and b) the detection of amplified sequences with a Cα probe.

The oligonucleotide belonging to a Cα segment used for the amplification can be, in particular, chosen from the sequences SEQ ID No. 54 and 55.

To check the efficiency of the amplification, the operation is preferably carried out in the presence of a pair of control primers and the corresponding control sequence amplified using a corresponding control probe is detected.

This pair of control primers can correspond to two Cβ segments, for example the CβF and CβK primers corresponding to sequences SEQ ID No. 59 and 61. Then a Cβ detection probe is used (corresponding for example to the sequence SEQ ID No. 62). But this pair of primers can also be constituted by two primers belonging to β-actin, notably those corresponding to sequences SEQ ID No. 57 and 58. Then a detection probe corresponding to a sequence of β-actin, such as the sequence SEQ ID No. 59, is used.

Also a subject of the present invention is a diagnostic kit for the implementation of the process defined previously, which includes:

a) at least one oligonucleotide chosen from the sequences SEQ ID No. 25 to 53, b) a Cα primer, c) a Cα probe.

In addition such a kit advantageously contains:

d) a pair of control primers, e) a control probe.

This kit can contain in particular:

a) the group of 29 oligonucleotides corresponding to sequences SEQ ID No. 25 to 53, b) a Cα primer chosen from the sequences corresponding to sequences SEQ ID No. 54 and 55, c) a pair of control primers for β-actin having a sequence corresponding to sequences SEQ ID NO. 57 and 58 respectively, d) a Cα probe corresponding to the sequence SEQ ID No. 56, e) a control probe for β-actin corresponding to the sequence SEQ ID No. 59.

In the information given in the list of sequences for the sequences 25 to 59, the sequences SEQ ID No. 25 to 46 correspond to sequences belonging to clones of known Vα1 to Vα22 sub-families (available from the EMBL database) or to sequences which differ from them by one or two nucleotides.

The sequences SEQ ID No. 48, 49, 50, 51 and 53 correspond to sequences belonging to clones of new sub-families of the invention, corresponding to sub-families provisionally designated Vαw24, Vαw25, Vαw26, Vαw27 and Vαw29 (w indicating that the designation is pending definitive designation).

The sequences SEQ ID No. 47 and 52 correspond to sequences belonging to clones IGRa01 and IGRa06 respectively of known sub-families but having not yet received definitive designation (Vα w23 and Vα w28 respectively) one member element of which has already been described (Hinkkanen A., et al. (31) and Bernard O. et al. (32) respectively). The complete sequence of IGRa06 has not yet been published.

The sequences SEQ ID No. 54 and 55 are two examples of oligonucleotides which can be used as Cα primers for amplification.

The sequence SEQ ID No. 56 is the sequence of a C probe which can be used for the detection of amplified DNAs.

The sequences SEQ ID No. 57, 58 and 59 are respectively the sequences of a pair of oligonucleotides belonging to the sequence of β-actin which can be used to check the amplification and the sequence of a probe for detecting the corresponding amplified DNAs.

In the list of sequences the position indicated is the position of the 5' end counting from the predicted initiation site of the ATG translation. In the case where the sequences are incomplete (unknown 5'region), the position (marked with an asterisk) is given relative to the first nucleotide of the sequence. The underlined nucleotides correspond to mismatches introduced relative to the natural sequence.

The oligonucleotides were synthesized with an Applied Biosystems 381 A automated DNA synthesizer using the β-cyano-ethylphosphoramidite method (Sinha N. et al. (33)) and following the protocol recommended by the manufacturer. The oligonucleotides were detritylated in the apparatus, cleaved from the support and deprotected with ammonia (at 60° C. for 5 hours). The crude products were purified by reverse phase high pressure chromatography on a μ-bondapak C18 column using an acetonitrile gradient (9 to 15%) in a 0.01M triethylammonium acetate buffer at pH 5.5.

The amplification carried out using the primers according to the invention can be, in particular, the technique of amplification by PCR (Polymerase Chain Reaction) as described by Saiki et al. (12) and in Patents U.S. Pat Nos. 4,683,195, 4,683,202, 4,889,818.

For the PCR, a double strand DNA can be used which is denatured or a cDNA obtained from RNA using reverse transcriptase as mentioned above.

The polymerization agent is a DNA polymerase, in particular, Taq polymerase.

Generally the amplification cycle is repeated 24 to 39 times.

The probes which are used for detecting the amplified sequences can be obtained by labelling the oligonucleotides with radio-active isotope, which leads to detection by autoradiography, or by conjugation with an enzyme such as peroxidase (ECL Amersham system), alkaline phosphatase or β-galactosidase (Tropix Ozyme system), which leads to detection by chemiluminescence.

The following example illustrates the implementation of the detection process according to the invention.

The peripheral lymphocytes of a healthy individual were prepared by density gradient centrifugation. The total DNA was extracted according to a one-stage method by extraction with guanidium isothiocyanate, phenol and chloroform (Chomczynski, 11). The complementary DNA was synthesized in a final volume of 20 μl at 42° C. for one hour using 1 to 5 μg of total RNA, the reverse transcriptase and the CαB primer (1.25 μM).

The material obtained was then heated at 95° C. for 3 minutes before being subjected to an amplification according to the PCR technique using in parallel each of the specific Vα primers corresponding to sequences SEQ ID No. 25 to 53 and the CαB primer specific to the Cα region (SEQ ID No. 55). This amplification was carried out in a final volume of 10 μl per tube containing 50 mM of KCl, 10 mM of tris-HCl pH 8.3, 1.5 mM of $MgCl_2$, 0.1% (weight/volume) of gelatine, 200 μM of dNTP, 0.25 units of Taq polymerase and 0.25 μM of each primer. A control amplification was carried out in each tube from 25 mN of a DNA fragment of β-actin of 877 base pairs prepared by PCR and Act 1 and Act 2 primers (SEQ ID No. 57 and 58) specific to actin. 30 amplification cycles were carried out followed by a final elongation stage of 5 minutes at 72° C. Each cycle included a denaturation stage at 94° C. for one minute, a hybridization stage at 65° C. for one minute and an elongation period at 72° C. for one minute.

The products obtained were separated by electrophoresis on 2% agarose gel, transferred onto nylon membranes in an alkaline buffer and hybridized simultaneously with the CαC oligonucleotide probes (SEQ ID No. 56) and Act 3 (SEQ ID No. 59) labelled with $^{32}P$ by the polynucleotidyl T4 kinase enzyme. The hybridization was carried out at 42° C. for 16 hours in a buffer containing 6×SSC, 0.5% SDS, 5×Denhardt's, 0.05% $NaH_2PO_4$ and 100 μg/ml of denatured salmon sperm DNA. The membranes were then washed with SSC 6×, 20 mM $NaH_2PO_4$, twice at ambient temperature for 5 minutes and once at 50° C. for 30 minutes then autoradiographed.

Figure 4:
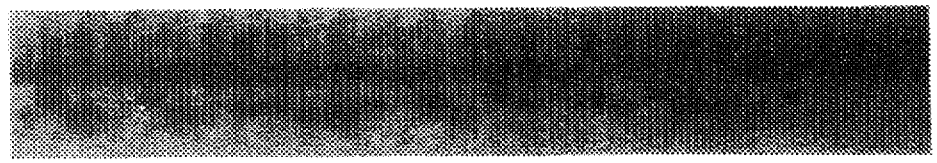
FIG. 4 represents the detection by autoradiography of amplified transcripts of TCR α chains expressed by the peripheral lymphocytes of a healthy individual and of a co-amplified β-actin control.

The results obtained are shown in FIG. 4.

The actin control (band of 877 base pairs) allows the amplification to be verified in all wells. A specific signal appears below this band the size of which corresponds to the size of corresponding amplified fragments, each fragment having a length corresponding to the distance between the locus of the specific Vα oligonucleotide and the Cα primer.

With the individual tested, FIG. 4 shows the preferential expression of certain genetic segments defined relative to the others. For example, the Vα27, 28 and 29 sub-families are less well represented than the Vα2, 3 and 6 sub-families.

REFERENCES

1. Meuer, S. C., et al., J. Exp. Med. 1983. 157:705.
2. Moingeon, P., et al., Nature 1986a. 323:638.
3. Brenner, M. B., et al., Nature 1986. 322:145.
4. Bank, I., et al., Nature 1986. 322:179.
5. Davis, M. M., et al., Nature 1988. 334:395.
6. Crews, S., et al., Cell 1981. 25:59.
7. Concannon, P., et al., Proc. Natl. Acad. Sci. USA. 1986. 83:6598.
8. Kimura, N., et al., Eur. J. Immunol. 1987. 17:375.
9. Wilson, R. K., et al., Immunological Reviews 1988c. 101:149.
10. Chirgwin, J. M., et al. Biochemistry 1979. 18:5294.
11. Chomczynski, P., et al., Anal. Biochem. 1987. 162:156.
12. Saiki, R. K., et al., Science 1988. 239:487.
13. Loh, E. Y., et al., Science 1989. 243:217.

14. Sanger, F., et al., Proc. Natl. Acad. Sci. USA 1977. 74:5463.
15. Lipman, D. J., et al., Science 1985. 227:1435.
16. Kozak, M., Nucl. Acids Res. 1984. 12:857.
17. Kyte, J., et al., R. F., J. Mol. Biol. 1982. 157:105.
18. Triebel, F., et al., J. Immun. 1988. 140:300.
19. Feinberg, A. P., et al., Anal. Bichem. 1983. 132:6.
20. Mengle-Gaw, L., et al., The EMBO Journal, 1987. 6:2273.
21. Klein, M. H., et al., Proc. Natl. Acad. Sci. USA 1987. 84:6884.
22. Yoshikai, Y., et al., J. Exp. Med. 1986. 164:90.
23. Wandenbark, A., et al., Nature, 341, 541.
24. Janeway, C., Nature, 341, 482.
25. Li, Y., J. Exp. Med., 171, 221.
26. Acha-Orbea, H., EMBO Journal, 1990.9, 12, 3815.
27. Kappler, J., Science 244, 811.
28. Choi, Y., PNAS, 86, 8941.
29. Nitta T. et al., Science 1990, 249, 672.
30. Sottini A. et al., Eur. J. Immunol., 1991, 21, 461.
31. Hinkkanen A. et al., Immunogenetics, 1989, 29, 131.
32. Bernard O. et al., Oncogene, 1988, 2, 195.
33. Sinha N. et al., Nucleic Acids Res. 1984, 12, 4539.

We claim:

1. Oligonucleotides selected from the group consisting of sequence SEQ ID Nos. 25 to 53.

2. In a method of amplification of DNA using a primer, the improvement comprising performing nucleic acid amplification using as primer a nucleotide sequence of about at least 17 nucleotides with a sequence of V α segment selected from the group consisting of SEQ ID Nos. 2 to 5, No. 11, neuclotides 1 to 200 of SEQ ID No. 1,
nucleotides 1 to 467 of SEQ ID No. 6,
nucleotides 1 to 77 of SEQ ID No. 7,
nucleotides 1 to 151 of SEQ ID No. 8,
nucleotides 291 to 386 of SEQ ID No. 9,
or a fragment of a J α segment,
selected from the group consisting of SEQ ID Nos. 12, 13, or 14 to 19.

3. In a method of amplification of DNA using a primer, the improvement comprising performing nucleic acid amplification using as primer, one of the nucleotide sequences of SEQ ID Nos. 25 to 53.

4. The method of claim 3 wherein the SEQ ID Nos. are one of 48, 49, 50, 51 and 53.

5. A process for detecting nucleotide sequences coding for V α segments of T-receptors or cDNA of transcription products thereof comprising in a biological sample, a) amplifying DNA with at least one pair of primers formed by one nucleotide selected from the SEQ ID Nos. 26 to 54 and any nucleotide sequence of about 17 nucleotides of a C α segment and b) detecting the amplified sequences with a C α probe.

6. The process of claim 5 wherein the amplification is performed in the presence of a pair of control primers and the detecting step is performed with a control probe.

7. A diagnostic kit comprising a) at least one oligonucleotide selected from the group consisting of SEQ ID Nos. 25 to 53, b) a C α primer and c) a C α probe.

8. A diagnostic kit of claim 7 also containing d) a pair of control primers and e) a control probe.

9. A kit of claim 8 wherein a) the oligonucleotides are the group of sequences consisting of SEQ ID Nos. 26 to 54, b) the C α primer is selected from the group consisting of SEQ ID Nos. 54 and 55, c) the C α probe is SEQ ID No. 56, d) the pair of control primers consists of SEQ ID Nos. 57 and 58 wherein the primers are specific for β-actin and e) the control probe consists of SEQ ID No. 60 wherein the control Probe is specific for β-actin.

* * * * *